(12) United States Patent
van der Krieken et al.

(10) Patent No.: US 11,317,631 B2
(45) Date of Patent: May 3, 2022

(54) NATAMYCIN COMPOSITIONS AND USES THEREOF

(71) Applicant: Arec Crop Protection B.V., Wageningen (NL)

(72) Inventors: Wilhelmus Maria van der Krieken, Wageningen (NL); Kieran P. Furlong, Dublin (IE)

(73) Assignee: Arec Crop Protection B.V., Wageningen (NL)

( * ) Notice: Subject to any disclaimer, the term of this patent is extended or adjusted under 35 U.S.C. 154(b) by 0 days.

(21) Appl. No.: 16/094,815

(22) PCT Filed: Apr. 18, 2017

(86) PCT No.: PCT/NL2017/050248
§ 371 (c)(1),
(2) Date: Oct. 18, 2018

(87) PCT Pub. No.: WO2017/183972
PCT Pub. Date: Oct. 26, 2017

(65) Prior Publication Data
US 2019/0116796 A1    Apr. 25, 2019

Related U.S. Application Data

(60) Provisional application No. 62/324,192, filed on Apr. 18, 2016.

(51) Int. Cl.
*A01N 43/90*    (2006.01)
*C07H 17/08*    (2006.01)
*A01N 25/14*    (2006.01)

(52) U.S. Cl.
CPC ............ *A01N 43/90* (2013.01); *A01N 25/14* (2013.01); *C07H 17/08* (2013.01)

(58) Field of Classification Search
CPC ........ A01N 43/90; A01N 25/14; A01N 25/34; C07H 17/08; A61K 31/7048
See application file for complete search history.

(56) References Cited

U.S. PATENT DOCUMENTS

| | | | |
|---|---|---|---|
| 5,821,233 A | 10/1998 | Van Rijn et al. | |
| 2003/0087003 A1* | 5/2003 | Ang | A23L 3/34635 426/61 |
| 2005/0042341 A1* | 2/2005 | Thomas | A21D 2/00 426/321 |
| 2008/0234210 A1* | 9/2008 | Rijn | A23B 7/155 514/28 |

FOREIGN PATENT DOCUMENTS

| | | |
|---|---|---|
| CN | 1280774 A | 1/2001 |
| CN | 102885056 A | 1/2013 |
| EP | 1068809 A2 | 1/2001 |
| EP | 1642500 A2 | 5/2006 |
| WO | WO 2006/045831 A1 | 5/2006 |
| WO | WO 2017/043972 A1 | 3/2017 |

OTHER PUBLICATIONS

Wendel, A. "Lecithin", Kirk-Othmer Encyclopedia of Chemical Technology, New York: John Wiley (Year: 2014).*
EPO machine translation of CN 102885056. (Year: 2013).*
Translated Office Action dated Jun. 28, 2020 of Chinese Application CN201780037967.9, 7 pages.
Gómez-Tena et al., Relationship between the specific surface area parameters determined using different analytical techniques, Qualicer 2014, Castellón (España), 10 pages.
Declaration of Wim van der Krieken in Chinese Patent Application No. 201780037967.9, dated Apr. 29, 2021, 3 pages.
Rawle et al., "Basic Principles of Particle Size Analysis", Malvern Instruments Limited, Technical Paper, 1993, 8 pages.

* cited by examiner

*Primary Examiner* — Leigh C Maier
(74) *Attorney, Agent, or Firm* — BakerHostetler

(57) ABSTRACT

Provided is a particular form of natamycin that shows improved properties as a fungicide for use in agricultural applications. A preferred natamycin composition comprises a structuring agent and a surfactant. Said natamycin composition further comprises cellular matter from a natamycin-producing organism. The natamycin in a natamycin composition preferably has a surface area of less than 6 $m^2/g$, and an average particle size of less than 6 micrometer. The invention further relates to methods, comprising contacting a plant or part thereof, a fungus, a fruit, a crop, a seed, and/or a soil with a natamycin composition of the invention.

18 Claims, 3 Drawing Sheets

US 11,317,631 B2

NATAMYCIN COMPOSITIONS AND USES THEREOF

CROSS REFERENCE TO RELATED APPLICATIONS

The present application is a 35 U.S.C. § 371 national phase application from, and claims priority to, International Application No. PCT/NL2017/050248, filed Apr. 18, 2017, which claims priority under 35 U.S.C. § 119(e) to U.S. Provisional Patent Application No. 62/324,192, filed Apr. 18, 2016. Each of these applications is incorporated by reference in its entirety herein.

FIELD

The present disclosure relates generally to natamycin, and more specifically to a particular form of natamycin that shows improved properties as a fungicide for use in agricultural applications.

BACKGROUND

Crop losses in the field attributable to molds can have significant impact of world crop production. Molds may also cause reduction in quality of crops such as loss of nutrients, off flavors and destruction of the tissue causing quality loss after processing. Mold infections may occur on plant tissue in the field, on seeds used for sowing, post-harvest and in the soil.

To prevent fungal damage of agricultural plants, synthetic fungicides and natural fungicides are on the market. However, several disadvantages are associated with the currently applied fungicides.

Many fungicides lose their activity over time due to fungi developed resistance to certain fungicides. Resistance can develop within a short period of time. Development of resistance results in an increase in the number of treatments and the application of higher amounts of the fungicide or the use of cocktails of two or more fungicides. Moreover, applying agrochemicals in high concentrations or using cocktails of agrochemicals often results in phytotoxic effects on the crop itself.

Many fungicides currently on the market cause harmful effects on the ecosystem, environment pollution and human health problems with respect to workers safety. In addition, high residue levels of harmful fungicides on agricultural products at the moment of consumption, even exceeding the maximum residue limits, present concerns.

Many natural antimicrobials, such as enzymes, bacterial cultures or plant extracts, generally lack effectiveness as compared with synthetic agrochemical fungicides. There is a need in the art to develop alternatives to harmful synthetic fungicides that not only combat harmful microorganisms, but also improve the development and yield of crops.

BRIEF SUMMARY

In some aspects, provided are natamycin compositions that have improved properties as a fungicide for use in agricultural applications. In certain aspects, provided are also fungicides made up of any of the natamycin compositions described herein.

In some embodiments, the natamycin composition has a surface area of less than 6 $m^2/g$. In some variations that may be combined with the foregoing, the natamycin composition is milled. When milled, in some variations, the natamycin composition has an average particle size of less than about 6 µm, preferably less than about 2 µm. In other embodiments, that may be combined with the foregoing, the natamycin composition comprises a structuring agent and a surfactant. In other embodiments, that may be combined with the foregoing, the natamycin composition further comprises cellular matter. In other embodiments that may be combined with the foregoing, the natamycin composition has improved solubility in water, thereby leading to improved bioavailability of the active ingredient, natamycin, in treatment against plant pathogens.

In other aspects, provided is a method that includes contacting a plant or a fungus, or a part thereof, with any of the natamycin compositions described herein to treat the plant or fungus, or a part thereof.

In other aspects, provided is a method that includes treating seeds with any of the natamycin compositions described herein; and germinating such treated seeds.

In yet other aspects, provided is a method that includes contacting fruit with any of the natamycin compositions described herein.

In yet other aspects, provided is a method that includes contacting soil with any of the natamycin compositions described herein. In some variations, the method includes contacting soil with any of the natamycin compositions described herein; and planting seeds in such soil.

In some variations of the foregoing, the method reduces or inhibits growth of at least one plant pathogen.

DESCRIPTION OF THE FIGURES

The present application can be best understood by reference to the following description taken in conjunction with the accompanying figures, in which like parts may be referred to by like numerals.

DETAILED DESCRIPTION

Figure 1A:
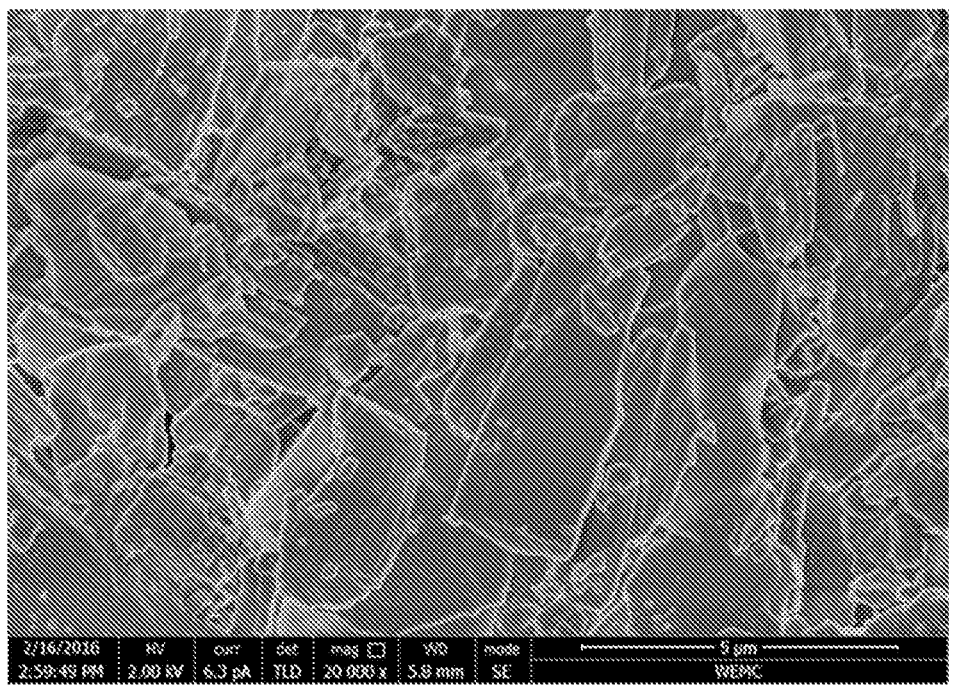
FIGS. 1A and 1B depict a SEM image (20,000×) of Natamycin Composition A n water (FIG. 1A) and Control Natamycin in water (FIG. 1B). The Natamycin Composition A and the Control Natamycin particles were suspended in water (250 g/l) and milled to an average particle size of 2 µm. After drying, the SEM images were taken.

The following description sets forth exemplary methods, parameters and the like. It should be recognized, however, that such description is not intended as a limitation on the scope of the present disclosure but is instead provided as a description of exemplary embodiments.

In some aspects, provided herein are natamycin compositions. Such natamycin compositions may be suitable for use as fungicides in agricultural applications. Thus, provided are also methods of using the natamycin compositions to treat plants, fungi, seeds, fruits, and soil.

A natamycin composition of the invention, comprising natamycin, or a salt thereof, wherein the natamycin composition has a surface area of less than 6 m²/g, and wherein the natamycin composition is milled. Said natamycin composition preferably comprises cellular matter of a natamycin producing microorganism, said cellular matter comprising remnants of a fermentation broth, remnants of a fermentation organism, and/or compounds excreted by the fermentation organism. Said composition was found to be more effective as a fungicide, when compared to a composition comprising purified natamycin at equal amounts of natamycin. In the absence of fatty acids, or in the presence of low amounts of fatty acids (<0.1% w/w fatty acid), a natamycin composition according to the invention was more effective in preventing outgrowth of fungi on treated plants, plant parts and/or soil, compared to a similar composition comprising a similar or identical amount of purified natamycin.

The term 'remnants", as is used herein, includes compounds that have remained in the cellular material, and modifications and derivatives of such compounds which were generated during the fermentation process and/or the extraction process.

In certain aspects, provided is a method that involves contacting a plant or a fungus, or a part thereof, with any of the natamycin compositions described herein to treat the plant or fungus, or a part thereof. In certain aspects, provided is a method that involves treating seeds with any of the natamycin compositions described herein to produce treated seeds; and germinating the treated seeds. In certain other aspects, provided is a method that involves contacting fruit with any of the natamycin compositions described herein. Such fruit may be pre- or post-harvest fruit. In yet other aspects, provided is a method that involves contacting soil with any of the natamycin compositions described herein, and planting seeds in the soil.

The natamycin compositions, and their uses and methods of preparation are described in further detail below.

Natamycin Composition

The natamycin compositions described herein include natamycin, or a salt thereof. Natamycin has the following chemical structure:

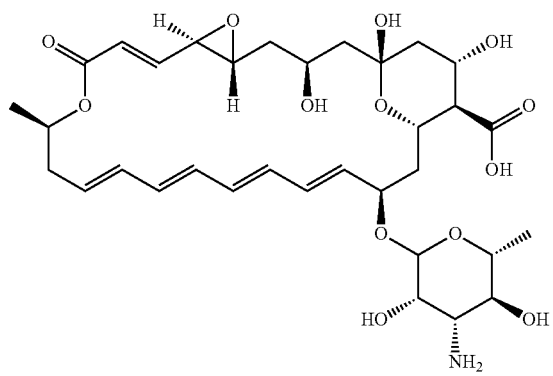 [SMILES: C[C@@H]1C/C=C/C=C/C=C/C=C/[C@H](OC2O[C@H](C)[C@@H](O)[C@H](N)[C@@H]2O)C[C@@H]2O[C@](O)(C[C@@H](O)C[C@H]3O[C@@H]3/C=C/C(=O)O1)C[C@H](O)[C@H]2C(=O)O]

A preferred natamycin composition comprising natamycin, or a salt thereof, wherein the natamycin composition has a surface area of less than 6 m²/g, and wherein the average size of the natamycin particles is reduced to less than 6 μm, preferably less than about 2 μm, for example by milling.

Methods for determining the average size of particles in a composition are known to the skilled person. For example, Hukkanen and Braatz, 2003. Sensors and Actuators B 96: 451-459, discuss varies methods that can be used for determining the average particle size in a composition, including forward light scattering and ultrasonic extinction. A preferred method is sieve analysis or laser diffraction analysis, for example using a Analysette 22-MicroTec plus laser-particle-sizer (Fritsch, Idar-Oberstein, Germany).

The natamycin compositions described herein may include additional components. For example, when the natamycin composition is produced by a fermentation process of natamycin-producing bacteria, in some embodiments, the natamycin composition may include cellular matter and/or other compounds produced from the fermentation process, or resulting from the fermentation process.

In some variations, the natamycin composition includes cellular matter. In certain variations, said cellular matter in the natamycin composition includes remnants of the natamycin-producing bacteria. In certain variations, said cellular matter in the natamycin composition includes compounds or remnants of compounds that were present in the growth medium of the producing bacteria. In certain variations, said cellular matter in the natamycin composition includes compounds excreted by the natamycin-producing bacteria. Examples of such compounds may include compounds of the bacterial cell envelope, which may include the plasma membrane and the cell wall of a bacterium.

In one variation, said cellular matter in the natamycin composition includes fragments of these cell envelope structures and/or individual compounds or building blocks of these cell wall and cell membrane structures. Such components of the cell wall may include, for example, peptidoglycans (poly-N-acetylglucosamine and N-acetylmuramic acid) or murein, teichoic acids (e.g., bacterial polysaccharides of glycerol phosphate or ribitol phosphate linked via phosphodiester bonds), glutamic acid, L, galactose, glucose, mannose, fructose, galactosamine, N-acetyl glucosamine, muramic acid, carbohydrates, ribitol, peptides, L-di-aminopimelic acid, glycine and alanine.

Said cellular matter in the natamycin composition may further include components of the cell membrane of the natamycin-producing bacteria. Such components of the cell membrane may include phospholipids and proteins. In one variation, the natamycin composition may include amphipathic lipids belonging to the classes of phospholipids, glycolipids and sterols. In another variation, the natamycin composition may include phosphatidylcholine, phosphatidylethanolamine, phosphatidylinositol and phosphatidylserine.

Said cellular matter in the natamycin composition may further include proteins such as membrane proteins, and amino acids. For example, such membrane proteins may be involved in cell-cell contact, surface recognition, cytoskeleton contact, signaling, enzymatic activity or transporting substances across the membrane of the natamycin-producing bacteria. In one variation, the natamycin composition includes hormones and carbohydrates. In another variation, the natamycin composition includes cerebrosides and gangliosides.

Said cellular matter in the natamycin composition may further include other bacterial compounds that may be present in a cellular extract, such as compounds and/or breakdown products which are part of the interior of the cell. Examples include compounds present in the cytoplasm, including nucleic acid molecules such as plasmids, DNA and RNA, ribosomes, intracellular membranes, enzymes, nutrient storage structures, such as glycogen, lipid structures, protein structures and sugar structures.

Said cellular matter in the natamycin composition may include other compounds present in the fermentation medium. Examples of such compounds include a protein nitrogen source (e.g., yeast extract, and/or non-yeast proteins such as protein hydrolysates, peptones, soy proteins, and beef extract); a metabolizable carbon source (e.g., glucose, molasses, lactose, polysaccharides, corn steep liquor, corn starch, and potato starch); growth factors (e.g., vitamins); inorganic elements (e.g., calcium, potassium, sodium, magnesium, ammonium sulphate); trace elements (e.g., zinc, copper, iron, boron and cobalt); and other breakdown products of the compounds of the fermentation medium.

The components of the natamycin composition may also vary based on the method or technique used to extract natamycin from a fermentation medium. For example, when an alcohol is used to disrupt cells in the fermentation broth, the natamycin composition may include natamycin alkylesters, such as natamycin methylester when methanol is used.

It should be understood that any of the components of the natamycin composition described herein may be combined as if each and every combination were individually listed. For example, in some embodiments, the natamycin composition includes natamycin, protein and starch or natamycin, natamycin alkylester, protein and starch, or natamycin, amino acids, nucleic acid molecules and starch, or natamycin, amino acids, peptidoglycans, nucleic acid molecules and starch.

The term protein, as is used herein, refers to oligo- or polyamino acid molecules comprising 5 or more amino acid residues up to 1000 amino acid residues.

The amount of various components in the natamycin composition may also vary. In some variations, the natamycin composition has between 1% and 90% by weight of natamycin. In other variations, at least 50%, at least 55%, or at least 60% by weight of the natamycin composition is natamycin, or a salt thereof. In other variations, between 50% and 65% by weight of the natamycin composition is natamycin, or a salt thereof. In other variations, between 1% and 5% by weight of the natamycin composition is a natamycin alkylester. The amount of natamycin present in the composition may depend on various factors, including how much natamycin was produced during fermentation and to what degree the composition was purified.

The amount of cellular matter in a crude natamycin composition may vary between 1 and 40% by weight, such as between 2 and 20% (w/w), preferably between 5 and 10% (w/w).

A composition of the invention further preferably includes at least one surfactant and at least one structuring agent.

Said surfactant preferably includes at least one anionic surfactant, or at least one non-ionic surfactant, or a combination thereof. Suitable anionic surfactants may include, for example, sodium lauryl sulphate; sulfosuccinate type of surfactants; ethoxylated tristyrylphenol salts, such as ethoxylated tristyrylphenol sulphate (e.g., 2,4,6-Tris[1-(phenyl)ethyl]phenylomega-hydroxypoly(oxyethylene) sulphate), and ethoxylated tristyrylphenol phosphate (e.g., polyethylene glycol 2,4,6-tristyrylphenyl ether phosphate triethanolamine salt); and sodiumdioctylsulphosuccinate; naphthalene sulphonate condensate; and styrene (meth) acrylic copolymer (e.g., which may include acrylamidopropyl methyl sulfonic acid monomers).

Suitable non-ionic surfactants may include, for example, poly(oxyethylene)-sorbitane-monolaurate, polymethyl methacrylate polyethylene glycol graft copolymer, ethylene oxide/propylene oxide block copolymers; and poly(oxyethylene)x-sorbitane-monolaurate. Any combinations of the surfactants described herein may be used.

A preferred combination comprises an ethylene oxide/propylene oxide block copolymer such as Atlas G 5002-L as non-ionic surfactant, and a styrene (meth)acrylic copolymer such as MetaSperse 550 S as an anionic surfactant.

The invention further provides a natamycin composition comprising natamycin, or a salt thereof, a structuring agent and a surfactant, wherein the natamycin composition further comprises cellular matter.

Said structuring agent preferably includes at least one of long chain polysaccharides, such as gellan gum, guar gum, succinoglycan gum (e.g., RHEOZAN®; Rhodia) and xanthan gum; mixtures of polysaccharides and glycoproteins such as arabic gom; a naturally occurring mineral such as attapulgite; and a polymer such as polyamide, polyacrylate, polyurethane, polyester and polyethylene (e.g., NEOCRYL® (DSM, The Netherlands)) and a co-polymer from said polymer.

Any combinations of the surfactants and structuring agents described herein may be used. In some variations, the surfactant(s) and structuring agent(s) may be present in the fungicide at a concentration of between 10 ppm and $2 \times 10^5$ ppm, or between 100 ppm and $10^4$ ppm, or between 500 ppm and 5000 ppm.

One or more of the surfactants described above, especially sodiumdioctylsulphosuccinate and naphthalene sulphonate condensate, may serve as wetting agents or dispersing agents. Thus, in certain variations, the fungicide includes at least one wetting agent, or at least one dispersing agent, or any combinations thereof. Suitable dispersing agents may include, for example, a naphthalene sulphonate condensate such as sodium alkylnaphthalenesulfonate, formaldehyde condensate (Morwet® D425). Suitable wetting agents may include groups of the phosphated di- or tristyrenephenol ethoxylates in the phosphate form and/or of lignin sulphonates; or ethoxylated tristyrenephenol phosphate, such as Soprophor® FL.

The pH of a natamycin composition according to the invention preferably is between pH=4 and pH=9, preferably between pH=5 and pH=8, most preferably between pH=5.5 and pH=6.5.

Surface Area

In some variations, the natamycin composition has a surface area of less than 6 m$^2$/g, less than 5 m$^2$/g, less than 4 m$^2$/g, less than 3 m$^2$/g, less than 2 m$^2$/g, or less than 1 m$^2$/g. In certain variations, the natamycin composition has a surface area between 1 m$^2$/g and 6 m$^2$/g, between 1 m$^2$/g and 3 m$^2$/g, or between 0.5 m$^2$/g and 3 m$^2$/g.

Surface area may be measured by any suitable methods or techniques known in the art. For example, with respect to the variations described above, the surface area is measured by BET (also known in the art as Brunauer, Emmett and Tellers analysis theory). Using BET analysis, the surface area of the natamycin composition may be determined by physical adsorption of nitrogen (N$_2$) gas on the surface of the natamycin composition, which is a solid. The value of the BET analysis is expressed as m$^2$ per gram of solid material.

Solubility

In some variations, the natamycin composition has a solubility in water of at least 1.5, at least 2, at least 3, at least 4, or at least 5 times greater than solubility in water of crystalline natamycin. In other variations, the natamycin composition has a solubility in water of between 2 and 4 times greater than solubility in water of crystalline natamycin. In one variation, the natamycin composition has a faster rate of dissolution in water as compared to crystalline natamycin. In one variation, crystalline natamycin has a well-defined geometrical crystalline form.

In certain variations, the natamycin composition has a solubility in water of at least 1.5, at least 2, at least 3, at least 4, or at least 5 times greater than solubility in water of pure natamycin. In other variations, the natamycin composition has a solubility in water of between 2 and 4 times greater than solubility in water of pure natamycin. In one variation, the natamycin composition has a faster rate of dissolution in water as compared to pure natamycin. In one variation, pure natamycin has a purity of greater then 90%, or greater than 95% by weight. In another variation, pure natamycin is in crystalline form. In yet another variation, pure natamycin has a well-defined geometrical crystalline form. FIG. 1B provides a SEM image of an exemplary sample of pure natamycin.

The term "pure natamycin", as used herein, refers to purified natamycin consisting of >90% natamycin, preferably ≥95% natamycin. Pure natamycin is characterized by having less than 5% of cellular matter, less than 4% of cellular matter, less than 3% of cellular matter, less than 2% of cellular matter, less than 1% of cellular matter, preferably by the absence of cellular matter, Cellular matter is defined as remnants of the natamycin-producing bacteria, compounds or remnants of compounds that were present in the growth medium of the producing bacteria, and/or compounds excreted by the natamycin-producing bacteria.

Solubility may be measured by any suitable methods or techniques known in the art. For example, with respect to the variations described above, solubility was measured by a high-performance liquid chromatography (HPLC) system with absorption chromatography.

It should be understood that any of the variations of the surface area, average particle size and solubility of the natamycin composition described herein may be combined as if each and every combination were individually listed. For example, in some embodiments, the natamycin composition has (i) a surface area of less than 3 $m^2/g$, (ii) an average particle size of less than 3 µm, and (iii) a solubility in water of at least 3 times greater than solubility in water of pure natamycin.

Bioavailability

In some variations, the natamycin composition has a bioavailability of at least 1.2, at least 1.5, at least 2, at least 3, at least 4, or at least 5 times greater than bioavailability of pure natamycin (>90% natamycin, preferably ≥95% natamycin). Bioavailability tests are known in the art. For example, a filter paper disc may be impregnated with a natamycin solution and positioned on an agar plate comprising a confluent layer of yeast. The plate is incubated for a first time period at a first temperature, for example 16 hours at 4° C., to allow solubilization of natamycin from the particles and diffusion of the solubilized natamycin into the agar plate. Subsequently, the plate is incubated for a second time period at a second temperature, for example 24 hours at 30° C., to allow growth of the yeast. The surface area surrounding the filter paper disc on which no growth of yeast can be scored is termed the inhibition zone as is a measure for the bioavailability of the natamycin. A suitable test is a Kirby-Bauer test, as described in Bauer et al., 1959. Arch. Int. Med. 104: 208-216; Bauer et al. 1966. Amer. J. Clin. Pathol. 45: 493-496; and U.S. Pat. No. 6,228,408B.

A natamycin composition, as defined herein, is produced by a fermentation organism and is only partially purified. The thus generated natamycin comprises remnants of the fermentation organism or fermentation broth and/or compounds excreted by the fermentation organism, which may result in the generation of an irregular crystal lattice in which crystals are mixed with said remnants and/or compounds. This irregular crystal lattice may result in the observed improved bioavailability and efficacy.

It should be understood that any of the variations of the surface area, average particle size, solubility and bioavailability of the natamycin composition described herein may be combined as if each and every combination were individually listed. For example, in some embodiments, the natamycin composition has (i) a surface area of less than 3 $m^2/g$, an average particle size of less than 3 µm, and (iii) a bioavailability of at least 2 times greater than the bioavailability of pure natamycin.

Particle Size

In certain variations, the mass median diameter (also referred to as D50) of the particles in the natamycin composition is less than 6 µm, less than 3 µm, or less than 2 µm, or about 2 µm.

When the average particle size of a natamycin composition is more than 6 µm, the average particle size of a natamycin composition preferably is reduced to an average particle size of less than 6 µm, preferably less than 2 µm. The natamycin composition can be crunched, for example milled, to achieve such particle sizes. The milling may result in more uniform, homogenous particle sizes. The natamycin compositions described herein can also be characterized by particle size distribution, which may be expressed using the average particle size and the particle size limits that describe 90% of the size of the particles. In some variations, the natamycin composition has: (i) an average particle size between 2 µm and 8 µm; and (ii) 90% of the particles have a particle size between 0.5 µm and 20 µm. In one variation, the natamycin composition has: (i) an average particle size between 5 µm and 10 µm, or between 7 µm and 8 µm; and 90% of the particles have a particle size between: 1 µm and 20 µm. In another variation, the natamycin composition has: (i) an average particle size between 1 µm and 2 µm, or between 1.7 µm and 1.9 µm; and 90% of the particles have a particle size between: 0.5 µm and 7.5 µm. In yet another variation, the natamycin composition has: (i) an average particle size between 1 µm and 3 µm, or about 2 µm; and 90% of the particles have a particle size between: 0.5 µm and 5.5 µm.

The natamycin in a preferred natamycin composition has an average particle size between 1 µm and 2 µm, whereby 90% of the particles have a particle size (d90) between 0.5 µm and 7 µm and with a surface area of less than 6 m2/g. The natamycin in a further preferred natamycin composition has an average particle size between 3 µm and 4 µm, whereby 90% of the particles have a particle size (d90) between 0.5 µm and 10 µm, with a surface area of less than 6 m2/g, comprising natamycin which has a bioavailability of at least 1.5 times greater than bioavailability of pure natamycin.

Other Characteristics

In some variations, the natamycin composition is solid. This solid material may be characterized by any suitable methods or techniques known in the art.

In some variations, the natamycin composition is formulated as a suspension concentrate, a water dispersible granule, a wettable powder, a suspo emulsion, an emusifiable concentrate, a dispersion concentrate, a water slurriable powder, a flowable seed treatment composition.

Figure 1B:
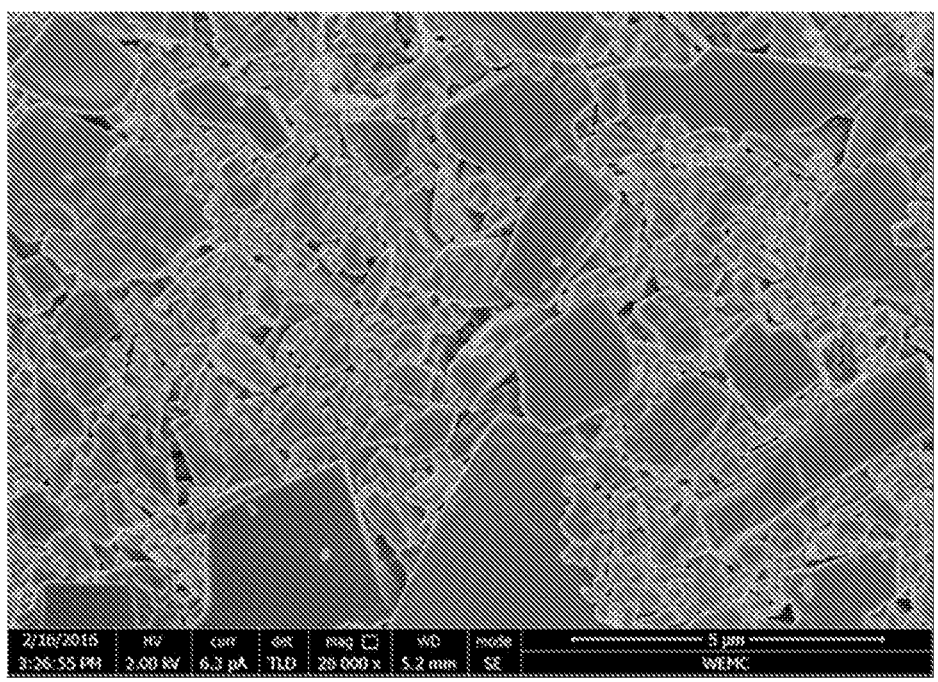

For example, with reference to FIG. 1A, the natamycin composition may be characterized by scanning electron microscopy (SEM).

Figure 2:
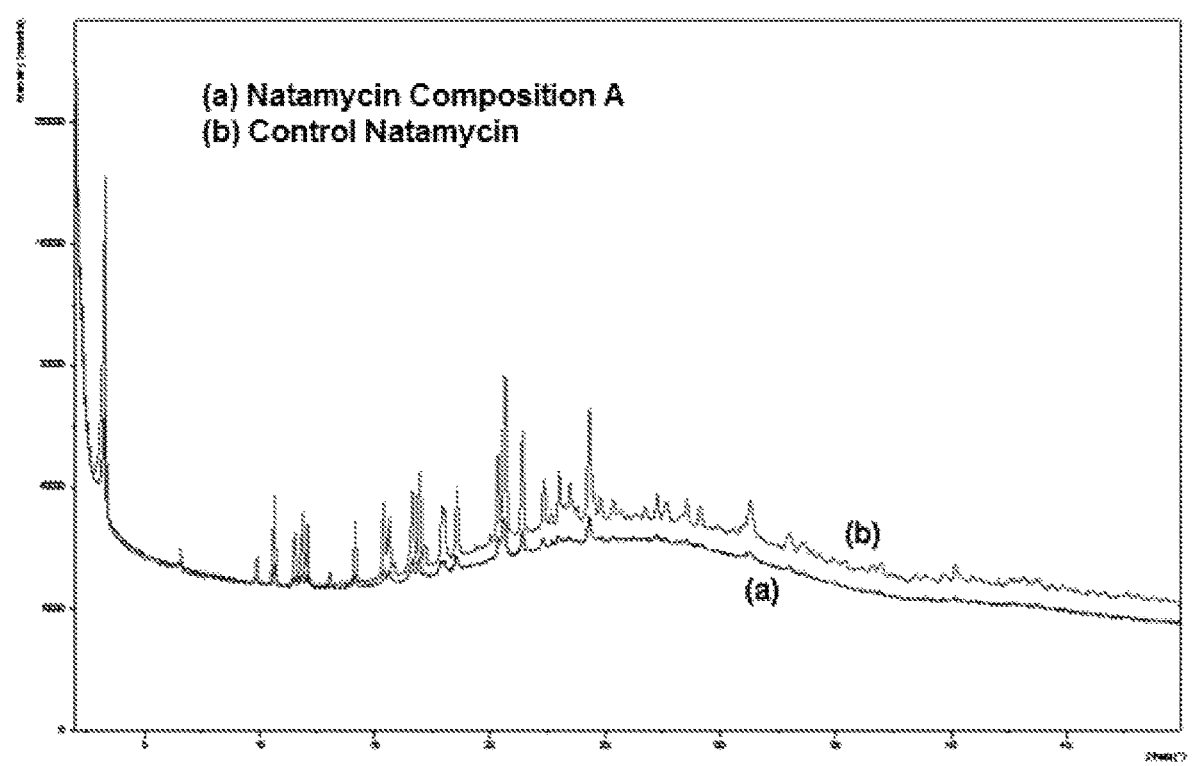
FIG. 2 depicts scaled powder XRD diffractograms of (a) Natamycin Composition A and (b) Control Natamycin. The Natamycin Composition A and the Control Natamycin particles were suspended in water (250 g/l) and milled to an average particle size of 2 µm in a bead mill (Dyno-mill® (Glen Mills Inc. Clifton, N.J.). The slurry was shaken thoroughly and taken up into a 0.5 mm glass capillary and measured with CuKα radiation in capillary mode. Y-axis denotes intensity (counts). X-axis denotes 2theta(°).

With reference to FIG. 2, the natamycin composition may also be characterized by X-ray diffraction (XRD) analysis.

The natamycin composition may also be characterized by differential scanning calorimetry (DSC) analysis, to study thermal transitions of the natamycin composition.

Uses of Natamycin Composition

The natamycin compositions described herein may be formulated for use as a fungicide in agricultural applications. In some embodiments, the natamycin composition is formulated as a fungicide for spraying onto plants, fungi, seeds, or fruits, or any parts thereof. The plants and fungi may refer to cultivated plants and fungi, e.g., for food, clothing, livestock, fodder, biofuel, medicine, or other uses. Such cultivated plants and fungi may be referred to as crops.

In some aspects, provided is a method for reducing or inhibiting growth of at least one plant pathogen. For example, in some variations, the plant pathogen is a fungal plant pathogen. In certain variations, the plant pathogen belongs to genus *Penicillium, Fusarium, Mierodochium, Rhizoctonia, Septoria, Botryotinia, Alternaria, Gibberella, Mycosphaerella,* or *Magnaporthe,* or any combinations thereof. In one variation, the plant pathogen is *Penicillium italicum, Gibberella fujikuroi, Magnaporthe grisea, Mycosphaerella fijiensis, Fusarium oxysporum, Fusarium graminearum, Colletotrichum musae, Fusarium pallidoroseum,* or *Fusarium proliferatum*. The natamycin compositions described herein may be used to treat a combination of plant pathogens. For example, in some embodiments, the natamycin composition reduces or inhibits growth of *Fusarium* spp. and *Microdochium* spp.

In one variation, provided is a method for reducing or inhibiting growth mold on fruit (e.g., citrus fruit, and banana), by contacting the fruit with the natamycin compositions described herein. In another variation, provided is a method for protecting a soil from a mold, by applying the natamycin compositions described herein to the soil.

In certain aspects, provided is a method for treating fungal plant diseases and molds, by contacting the natamycin compositions described herein with the plant, fungus, seeds, or fruits, or any parts thereof. In one variation, the plant disease is a soil-borne disease, or a seed-borne disease. In another variation, provided is a method for treating Black sigatoka, or Panama disease, by contacting the natamycin compositions described herein with the plant, fungus, seeds, or fruits, or any parts thereof. In some variations, the molds may grow on a crop in the field (e.g., pre-harvest), or may grow on harvested agricultural products (e.g., post-harvest). In one variation, provided is a method for treating a post-harvest disease, by contacting the natamycin compositions described herein with a plant, fungus or fruit, or any parts thereof.

Examples of plant diseases and molds that can be combatted with the natamycin compositions described herein include:

Soilborne diseases. One example of a soil-related mold disease is *Fusarium* wilt or Panama disease caused by *Fusarium oxysporum* f. sp. cubense. Other soilborne phytopathogenic fungi are for example other *Fusarium* species such as *Fusarium oxysporum* f. sp. *lycopersici* and *Fusarium oxysporum* f. sp. *fragariae, Rhizoctonia solani, Sclerotinia* species, *Pythium* species and *Pestalotiopsis clavispora*. In addition, major soil-borne pathogens on different crops are for cereals include, for example, *Gaeumanomyces graminis, Pseudocercosporella herptrichoides, Bipolaris sorokiniana* and *Polymyxa graminis*; for corn include, for example, *Fusarium moniloforme, Colletotrichum graminicola, Gibberella zeae* and *Macrophomina phaseolina*; for rice include, for example, *Sclerotium oryzae, Helminthosporium oryzae, Curvularia lunata, Bipolaris oryzae* and *Achlya* species; for cotton include, for example, *Fusarium oxysporum, Thielaviopsis basicola, Macrophomina phaeseolina* and *Glomerrella gossypii* for soybean, include for example, *Fusarium virguliforme, Phytophthora sojae, Sclerotium rolfsii, Macrophomina phaeseolina* and *Phialophora gregata*; for potato include, for example, *Rhizoctonia solani, Phoma* species, *Helminthosporium solani, Colletotichum coccodes, Fusarium sambucinum, Spongospora subterranean* and *Phytophthora erythroseptoca*. Examples of unwanted molds which may occur in mushroom growth substrate are, for example, *Trichoderma* species (e.g. *T. harzianum, T. aggresivum* and *T. viride*), *Verticillium* species (e.g. *V. fungicola* var. *fungicola* and *V. fungicola* var. *aleaophilum*), *Aspergillus* species, *Penicillium* species, *Dactylum* species (e.g. *D. dendroides*) and *Mycogone* species (e.g. *M. pernicosa*).

Seed-borne diseases and diseases on bulbs and tubers. Examples of mold diseases on flower bulbs such as tulip and lily are *Fusarium* species such as *Fusarium oxysporum, Botrytis* species, *Pythium* species, *Rhizoctonia* species and *Stagnospora* species. Examples of mold diseases on seed-potatoes are *Fusarium* species (e.g. *Fusarium solani*), *Rhizoctonia solani, Phoma* species, *Helminthosporium solani, Colletotichum coccodes* and *Penicillium* species. Key diseases occurring on seeds such as seed rot are caused by, for example, *Aspergillus* species (e.g. *A. terreus*), *Penicillium* species and *Phomopsis* species; the damping-off disease on seeds is caused by, for example, *Pythium* species, *Fusarium* species and *Rhizoctonia* species; the post-emerge disease may be caused by, for example, *Helminthosporium* species, *Ustilago* species and *Tilletia* species. The main seed-borne fungi on cereals include, for example, *Fusarium* species, *Alternaria* species, *Cochliobilus sativus, Stagnospora nodorum, Ustilago nuda* and *Claviceps purpurea*. Seed-borne fungi on soybean may include, for example, *Phomosis* species, *Diaporthe* species, *Peronospora manshurica, Cercospora kikuchii, Alternaria* species and *Fusarium* species. Seed-borne fungal pathogens on rice include, for example, *Fusarium* species, *Alternaria padwickii, Curvularia lunata, Bipolaris oryzae, Helminthosporium* species and *Pyricularia oryzae*. Seed-borne pathogens on corn include, for example, *Fusarium* species, *Penicillium* species, *Aspergillus* species, *Bipolaris* species, *Alternaria* species and *Rhizopus* species. On cotton seeds e.g. *Aspergillus* species, *Thielaviopsis* species and *Fusarium* species may develop.

Molds on a crop in the field (pre-harvest) Examples of leaf mold diseases on banana plants are Sigatoka leaf spot or yellow Sigatoka caused by *Mycosphaerella musicola* and Black Sigatoka caused by *Mycosphaerella fijensis*. An example of a disease on potato plants is early blight disease caused by *Alternaria* species such as *Alternaria solani* and *Alternaria alternate*. Another example of a disease on potato plants, but also applicable to tomato plants, is late blight disease caused by *Phytophthora infestans*. *Alternaria* species are also able to damage crops in the field such as vegetables, cotton, tobacco and cereals or may cause black spot disease on tomatoes, onions and carrots. *Fusarium oxysporum* is an example of a pathogenic mold on many crops such as corn and soya. Powdery mildew is an example of a disease on many crops which can be caused by different fungal species. Examples include *Erysiphe* species (e.g. *E. necatoron* grapes, *E. betae* on sugarbeet, *E. cruciferarum* on cabbage, *E. graminis* species on cereals), *Oidium lycopersicum* on e.g. tomato, *Podosphaera* species on e.g. rose, apple and strawberry, *Blumeria graminis* on wheat and barley, *Sphaerotheca fusca* on cucumber and melon and *Leveillula taurica* on paprika, pepper and aubergine. Downey mildew is another plant disease which can be caused by many different fungal species. Examples include *Plasmopara viticola* on e.g. grapevine,

*Pseudoperonospora humuli* on e.g. hop, *Peronospora parasitica* on e.g. cabbage, *Peronospora destructor* on e.g. onion, *Peronospora belbahrii* on e.g. basil, *Pseudoperonospora cubensis* on e.g. cucumber, melon or cantaloupe, *Pseudoperonospora farinosa* f.sp. *betae* on e.g. sugarbeet, *Bremia lactucae* on e.g. lettuce.

(4) Molds growing on harvested agricultural products (post-harvest). Molds which can develop on harvested fruit such as apples, pears, citrus fruit, stone fruit and berries are for example *Botrytis cinerea* on grapes and soft fruit, *Botrytis aclada* on onions, legumes and fruits, *Gloeosporium fructigenum, Gloeosporium perennans, Phytophthora cactorum, Phytophthora syringae, Penicillium* species (e.g. the mycotoxin patulin producing *P. expansum* on pomaceous fruits and nuts, *P. digitatum* and *P. italicum* on citrus fruit, *P. verrucosum* and *P. viridicatum* on cereals), *Fusarium moniloforme* on corn, *Rhizopus stolinifer* on strawberries. *Aspergillus flavus* has the ability to produce the mycotoxin aflatoxin, including in peanuts, pistachio nuts, Brazil nuts and corn. *Aspergillus fumigatus* may develop on a wide range of stored fruits, crops, cereals, cocoa beans and nuts. *Aspergillus pullulans* may develop on stored grains, strawberries, citrus fruit and cherries. Examples of fungal pathogens that may be found on pineapples include *Thielaviopsis paradoxa, Penicillium funicolosum, Fusarium oxysporum, Rhizophus stolonifer* and *Aspergillus niger*. On bananas, examples of disease after harvesting is crown rot, which can be caused by a number of fungal species: examples of fungal pathogens commonly found on bananas are *Colletotrichum musae, Thieliaviopsis paradoxa, Fusarium roseum, Verticillium theobromae, Lasiodiplodia theobomae* and *Deightoniella torulosa*.

In some variations, treating is an approach for obtaining a beneficial or desired result. In one variation, treating a disease may result in increasing the number of plants grown per area. In another variation, treating a disease may result in increasing plant or crop yield.

In other aspects, provided is a method for increasing plants or crops grown per area, by contacting the natamycin compositions described herein with a plant or seed, or any parts thereof. In some variations, the plants grown per area are increased as compared to a plant or seed, or any parts thereof, that is untreated. In other variations, the plants grown per area are increased as compared to commercial fungicides used in the art.

In yet other aspects, provided is a method for increasing plant or crop yield, by contacting the natamycin compositions described herein with a plant or seed, or any parts thereof. In some variations, the plant or crop yield is increased as compared to a plant or seed, or any parts thereof, that is untreated. In other variations, the plant or crop yield is increased as compared to commercial fungicides used in the art.

Commercial fungicides may include, in one variation, a fungicide comprising fludioxonil (e.g., Celest®, Syngenta); or, in another variation, a fungicide comprising prothioconazole (e.g., Redigo®, Bayer Crop Science).

Plants, Fungi and Parts Thereof

In some embodiments, the natamycin composition is contacted with a plant, or a part thereof. Suitable plants include, for example, a sugar beet plant, an onion plant, a tomato plant, a potato plant, a wheat plant, a soybean plants, a grapevine, a citrus plant, a banana plant, or a corn plant.

In certain embodiments, the natamycin composition is contacted with a part of plant. In one variation, the plant part is a leaf, stem, seed, bulb (including, e.g., flower bulb), seed-potato, root, tuber (including, e.g., root tuber), fruit, vegetable, rootstocks, and cuttings.

In other embodiments, the natamycin composition is contacted with a fungus, or a part thereof. Suitable fungi may include, for example, mushroom.

In some variations, the natamycin composition is contacted with seeds. Thus, in one variation, the natamycin composition is formulated for seed treatment. Suitable seeds may include, for example, seeds of cereals (e.g., corn, wheat, barley, rice, sorghum, oats, rye); nuts (e.g., peanuts, coffee, cacao, almonds, pistachios); leguminous plants (e.g., soy beans, beans) vegetables (e.g., lettuce species, cabbage species, broccoli, spinach, tomatoes, paprika, cucumbers, onions); fruit plants (e.g., grapes, citrus fruit, apples, pears, stone fruit); ornamental plants (e.g., roses, chrysanthemum, geranium, petunia, begonia); fibrous plants (e.g., cotton); oleaginous plants (e.g., rapeseed, sunflower, cocoa, ground-nuts); flowers (e.g., rose, lily, orchid). Example of bulbous or tuberous plants are flower bulbs (e.g., tulip, lily, hyacinth, crocus, narcissus), seed-potatoes and onions. An example of a root tuber is a dahlia.

In one variation, the seeds are wheat seeds or soybean seeds. The seeds may include seeds for growing of new plants, as well as seeds stored as feed or food.

In some variations, the natamycin composition is contacted with fruit, or a part thereof. In one variation, the natamycin composition is contacted with fruit, or a part thereof, as the fruit grows on the plant. In another variation, the natamycin composition is contacted with fruit, or a part thereof, post-harvest. Suitable fruit include, for example, citrus fruit (e.g., orange, lemon, lime), banana, apples or pineapples.

In other variations, the natamycin composition may be contacted with crops in a field. For example, such crops may be sprayed. Further, such crops may be sprayed at various times in the agricultural process, e.g., before or after harvesting. For example, crops may be sprayed preventively before a mold infection develops; after a mold infection developed; before, during or after flowering; before, during, or after fruit, nuts and grains develop. In situations where the risk of infection is high, e.g., during a rain season for tropical crops or in case of bad weather conditions, the natamycin composition can be applied more regularly. When the risk of infection is lower, spray intervals may be longer. Harvested crops such as fruits, vegetables, flowers and nuts can be treated using any suitable methods known in the art, and as described herein, including, for example, by immersing or spraying at any time after harvesting. Examples of crops include cereals (e.g., corn, wheat, barley, rice, sorghum, oats, and rye); tropical fruit (e.g., banana, pineapple, papaya, kiwi and mango fruit); citrus fruit (e.g., oranges, lemons, limes, mandarins and grapefruits); pome fruits (e.g., apples and pears); stone fruit (e.g. peaches, cherries, almonds, plums and apricots); berries (e.g., strawberries, raspberries, blackberries and currants); vegetables (e.g., lettuce, cabbage, tomatoes, cucumbers, paprika, peppers, onions, carrots, potatoes); leguminous plants (e.g., beans, peas, soy beans); oleaginous plants (e.g., rapeseed, sunflower, cocoa, ground-nuts, coconut); cucurbitaceae (e.g., cucumber, aubergines, melons, pumpkins); fibrous plants (e.g., cotton); ornamental plants, trees and flowers (e.g., tulip, lily, rose, orchids, chrysanthemum, petunia, begonia, violet, dahlia, fuchsia, gerbera, narcissus, crocus, conifers); and other crops such as coffee, tea, rubber, grapevines, nuts, pistachios, tobacco, conifers, sugarcane, sugar beet, fodder beet and hop.

Modes of Contact

The natamycin composition may be contacted with the plants, fungi, seeds, and fruits, or any parts thereof, using any suitable method known in the art. The natamycin composition may be applied by, for example, spraying plants in the field or in greenhouses optionally using a carrier such as a wax or an oil; dipping seeds, bulbs or seed-potatoes; adding to a plant part such as a seed or root system, e.g. via the soil; adding to a plant part such as a seed, seed-potato or bulb via a seed coating or a seed dressing; adding to the soil or growth substrate in which the seeds are to be planted or germinating and/or plants or mushrooms are developing; adding to water or watering systems applied in e.g. greenhouses or in the field; treating harvested plant parts such as bulbs, seeds, cereals, soybeans, flowers, fruit, vegetables or plants by, for example, dipping or spraying.

In some variations, the natamycin composition may be formulated for immersion, dipping, watering, injecting in the soil, drenching, vaporizing, spraying, electrostatic spraying, fogging, fumigating, brushing, painting and mixing. For example, when used to protect a crop in the field or in a greenhouse, a natamycin composition may be applied as an aqueous or oil suspension or solution by spraying or fogging. When applied post-harvest, the natamycin composition may be applied by immersion, fogging or spraying. The natamycin composition may also be applied via a watering system or by using a carrier such as a coating, dressing or wax.

In one variation, the natamycin composition may be sprayed. In such a variation, the natamycin composition may be formulated as a fungicide spray. For example, an airbrush may be used to spray the natamycin composition. In certain variations, the natamycin composition is applied by spraying plants in a field.

In another variation, seeds may be treated with the natamycin composition. Any suitable methods or techniques known in the art may be used to treat seeds. For example, in certain variations, the natamycin composition is used to prepare a seed dressing or a seed coating.

In yet another variation, the natamycin composition is used to prepare a coating emulsion, e.g., for use on fruit or plants in the field. In yet another variation, the natamycin composition is used to prepare a wax that is applied on fruit.

In yet another variation, seeds and/or fruits may be immersed in the natamycin composition. Any suitable methods or techniques known in the art may be used to immerse seeds and/or fruits seeds.

In yet other variations, the natamycin composition is contacted with soil. Any suitable methods or techniques known in the art may be used to contact the natamycin composition with the soil. In one variation, spraying or mixing may be employed. In another variation, the natamycin composition may be applied using a watering system, or by incorporation with fertilizers or nutrient granules applied to the soil. The natamycin composition may reduce development of pathogenic fungi.

Formulation

When the natamycin composition is formulated as a fungicide, the natamycin composition may include other compounds or agents. In some embodiments, the fungicide includes co-formulants like surfactants, sticking agents, antifoaming agents, thickening and stabilizing agents, biocides, and film formers such as propylene glycol and glycerol.

Any combinations of the surfactants described herein may be used. In some variations, the surfactant(s) may be present in the fungicide at a concentration of between 10 ppm and $2 \times 10^5$ ppm, or between 100 ppm and $10^4$ ppm, or between 500 ppm and 5000 ppm.

In other variations, the fungicide further includes at least one sticking agent. Suitable sticking agents may include latex-based products (e.g., PROLONG® (Holland Fyto B. V., The Netherlands) and BOND® (Loveland Industries Ltd)); pinolene/terpene-based products (e.g., NU-FILM® (Hygrotech Saad) and SPRAY-FAST® (Mandops)); and a hydrated magnesiumaluminum silicate, such as attapulgite (e.g., Attagel®; BASF).

Any combinations of the sticking agents described herein may be used. In certain variations, the sticking agent(s) may be present in the fungicide at a concentration of between 10 ppm and $10^5$ ppm, or between 100 ppm and $10^4$ ppm, or between 500 ppm and 5000 ppm.

In certain embodiments, the fungicide further includes water. In some variations, the fungicide is aqueous. In other variations, the fungicide is non-aqueous. In one variation, the fungicide is a concentrated stock that has to be diluted with a suitable diluent, such as water or oil. In another variation, the fungicide is an aqueous or non-aqueous ready-to-use composition.

In other embodiments, the natamycin composition may be formulated as a dry composition, such as a granulate, a powder, or a tablet. Such dry composition may be a concentrated dry composition, which can be used to prepare compositions for immersions, or spraying or dipping of agricultural products.

In certain embodiments, the natamycin composition is formulated as a suspension concentrate, a water dispersible granule, a wettable powder, a suspo emulsion, an emusifiable concentrate, a dispersion concentrate, a dry powder seed treatment composition, a water slurriable powder, a flowable seed treatment composition, or a water dispersible granule seed treatment composition.

The natamycin composition may be formulated for use without dilution or after dilution. In one variation, the natamycin composition is formulated as a suspension of solid particles in a liquid intended for dilution with water prior to use. In another variation, the natamycin composition is formulated as a dispersion of solid particles in a liquid intended for dilution with water prior to use. In another variation, the natamycin composition is formulated in granule form that is dispersible in water, forming a dispersion such as a suspension or solution. In yet another variation, the natamycin composition is formulated as a powder for mixing with water or another liquid prior to use. In yet another variation, the natamycin composition is formulated as a powder that is made into a slurry in water prior to use.

Dosage

In some variations, a dosage of the natamycin composition refers to the volume of the natamycin composition applied to (i) a surface area of a field in spray applications, (ii) a set mass of seed (e.g., 100 kg of seeds, also referred to in the art as "Q"), (iii) a surface area of land for soil treatment, or (iv) a defined mass of food product or post-harvest crop. In other variations, a dosage of the natamycin composition refers to the concentration of formulation or active ingredient in a solution to be used for immersing a food product or post-harvest crop.

The dosages selected may depend on various factors, including, for example, the formulation; the mode of contact; the type of plant, fungus, seed or fruit; and the type of plant pathogen or disease.

Methods of Producing Natamycin Composition

Provided are also methods for producing the natamycin compositions described herein. The natamycin composition may be produced by a fermentation process of natamycin-producing bacteria. In some aspects, provided is a method for producing a natamycin composition, by:

providing a fermentation broth comprising natamycin;

filtering the fermentation broth to obtain a filtration cake, wherein the filtration cake comprises natamycin;

contacting the filtration cake with an organic solvent to dissolve at least a portion of the natamycin present in the filtration cake and produce a natamycin solution; and precipitating a natamycin composition from the natamycin solution.

The fermentation broth may be produced by a suitable fermentation process using natamycin-producing bacteria. Such bacteria may include, for example, *Streptomyces natalensis* and *Streptomyces gilvosporeus*.

Any suitable medium for fermentation of a specific production strain can be applied. For example, the fermentation medium contains sufficient feed sources and nutrients, such as metabolizable carbon and nitrogen sources, growth factors, inorganic elements and trace elements. The medium for fermentation may be prepared in water and may include a combination of one or more of the following compounds:

a nitrogen source such as yeast extract and/or non-yeast proteins, such as protein hydrolysates, peptones, soy proteins, beef extract;

a metabolizable carbon source such as glucose, molasses, lactose, polysaccharides, corn steep liquor, corn starch, and potato starch;

growth factors such as vitamins;

inorganic elements such as calcium, potassium, sodium, magnesium, ammonium sulphate; and/or trace elements such ad zinc, copper, iron, boron and cobalt.

The fermentation medium may further include anti-foaming agents such as silicone defoamer to control foaming during the fermentation.

The fermentation may be carried out in any suitable fermentation vessel, using any suitable techniques or methods known in the art. For example, the fermentation medium may be brought to a suitable temperature, for example between 28°-35° C., inoculated with a production strain, and incubated for a sufficient period of time. The fermentation time may depend upon various factors, including the composition of the fermentation medium, the incubation temperature, the oxygen supply, the stirring equipment, the quality of the inoculum and the development of the fermentation. For example, the fermentation time may 60 to 170 hours.

During the fermentation oxygen and/or air is supplied to maintain a suitable level of dissolved oxygen in the fermentation medium during the main part of the fermentation, a feed source such as the carbon source is supplied at a sufficient rate and the pH may be controlled.

A natamycin composition can be recovered from the fermentation broth using different methods. For example, in some variations, the fermentation broth, including the fermentation medium and cells of the production organism, is treated to eliminate at least a portion, or all, living cells of the production organism. Elimination of the cells of the production organism may also be executed after one or more processing steps such as processing steps required to concentrate the fermentation broth through any suitable method such as evaporation, filtration and centrifugation. To improve evaporation or filtration, the fermentation broth may be heated. For example, in one variation, the fermentation broth is heated to a temperature between 50-70° C.

The natamycin composition may be prepared by using one or more organic solvents, either alone or in combination with adjustment of the pH to dissolve or precipitate the natamycin fraction. In addition, one or more filtration, elution and/or extraction steps can be added. Examples of suitable organic solvents include ethanol, methanol, butanol, propanol, isopropanol or any combinations of organic solvents. In addition, salts such as $CaCl_2$ and NaCl may be added to improve the recovery process, while acetone and salts such as ammonium sulfate may be used for salting out the fermentation broth.

The disintegration of the biomass can be realized using any method known in the art. Other examples of such methods for lysis of the producing cells include, for example, the use of a heat treatment step that is carried out for a sufficient period of time at a sufficient temperature; a pH treatment by adding compounds to increase or decrease the pH to values resulting in an alkaline or acid incubation of the fermentation broth; the use of antimicrobial agents; using surface active agents such as cell wall degrading enzymes or chemical surfactants to damage the cell membrane of the production organism; the use of disruption technologies such as homogenization, ultrasonic treatment, electrostatic treatment, magnetic field, high shear mixing, etc.; any combination of an organic solvent and one or more of the methods described above can be applied to generate natamycin. The disintegration of the biomass may result in lysis and destruction of all cells of the production strain. In addition, disintegration may result in fragmentation of the cellular structures, especially the hyphae and in solubilisation of cell constituents. Various methods and techniques are known in the art to check the disintegration of cells of the production organism, e.g. by microscopy, measuring the viscosity of the biomass, or determining development of colonies on a suitable growth medium on an agar plate.

In some variations, provided is a method of producing a natamycin composition, by:

providing a fermentation broth comprising natamycin;

filtering the fermentation broth to obtain a filtration cake, wherein the filtration cake comprises natamycin;

treating the filtration cake with an organic solvent;

dissolving at least a portion of the natamycin in the treated filtration cake to produce a natamycin solution;

optionally extracting, filtering, and/or eluting the natamycin solution;

precipitating at least a portion of natamycin from the natamycin solution to obtain a natamycin composition; and optionally separating and/or drying the natamycin composition.

In certain variations, the organic solvent used to treat the filtration cake includes an alcohol. In one variation, the alcohol is methanol, ethanol, isopropanol or propanol.

In certain variations, the dissolving of at least a portion of the natamycin in the treated filtration cake comprises increasing the pH of the treated filtration cake. In one variation, the pH is increased to about pH 10. Any suitable bases may be used to increase the pH. For example, a suitable base is sodium hydroxide (NaOH). When a base is used, then the precipitating of at least a portion of natamycin from the natamycin solution comprises adding an acid to obtain a pH of about 6-7. Such acid may include, for example, hydrochloric acid (HCl).

In other variations, the dissolving of at least a portion of the natamycin in the treated filtration cake comprises reducing the pH of the treated filtration case. In one variation, the pH is reduced to about pH 3. Any suitable acids may be used to reduce the pH. For example, a suitable acid is hydrochloric acid (HCl). When an acid is used, then the precipitating of at least a portion of natamycin from the natamycin solution comprises adding a base to obtain a pH of about 6-7. Such base may include, for example, sodium hydroxide (NaOH).

In other aspects, provided is a method of producing a natamycin composition, by:
  providing natamycin;
  dissolving the natamycin at a pH of at least 10 to produce a natamycin solution;
  adding saccharides, proteins, starch, or surfactants, or any combinations thereof, to the natamycin solution;
  precipitating at least a portion of natamycin from the natamycin solution to obtain a natamycin composition; and
  optionally separating and/or drying the natamycin composition.

In other aspects, provided is a method of producing a natamycin composition, by:
  providing natamycin;
  dissolving the natamycin at a pH of less than 3 to produce a natamycin solution;
  adding saccharides, proteins, starch, or surfactants, or any combinations thereof, to the natamycin solution;
  precipitating at least a portion of natamycin from the natamycin solution to obtain a natamycin composition; and
  optionally separating and/or drying the natamycin composition.

In yet other aspects, provided is a method of producing a natamycin composition, by:
  providing natamycin;
  dissolving the natamycin in an organic solvent;
  adding saccharides, proteins, starch, or surfactants, or any combinations thereof, to the natamycin solution; and
  solidifying the natamycin solution by freeze drying or spray drying.

In some variations, the organic solvent includes an alcohol or an ether, or any combinations thereof. For example, the organic solvent may include, methanol, ethanol, dimethyl sulfoxide (DMSO), t-butanol, and petroleum ether. A combination of organic solvents may also be used.

In variations of any of the foregoing methods, the methods further include milling the natamycin composition in the presence of formulating agents to produce a formulated natamycin composition. Such formulating agents may include, for example, surfactants, antifoaming agents, thickening agents, stabilizing agents, or glycerol, or any combinations thereof.

For the purpose of clarity and a concise description, features are described herein as part of the same or separate aspects and preferred embodiments thereof, however, it will be appreciated that the scope of the invention may include embodiments having combinations of all or some of the features described.

Illustrative Embodiments

Provided here are illustrative embodiments of the disclosed technology. These embodiments are illustrative only and do not limit the scope of the present disclosure or of the claims attached hereto.

Embodiment 1. A natamycin composition comprising natamycin, or a salt thereof, wherein the natamycin composition has a surface area of less than 6 m$^2$/g, and wherein the natamycin composition is milled.

Embodiment 2. The natamycin composition of embodiment 1, wherein the natamycin composition has a surface area of less than 2 m$^2$/g.

Embodiment 3. The natamycin composition of embodiment 1 or 2, wherein the natamycin composition has a solubility in water of at least 1.5 times greater than solubility in water of pure natamycin.

Embodiment 4. The natamycin composition of any one of embodiments 1 to 3, wherein the natamycin composition has a bioavailability of at least 1.5 times greater than bioavailability of pure natamycin.

Embodiment 5. The natamycin composition of any one of embodiments 1 to 4, further comprising at least one surfactant and at least one structuring agent.

Embodiment 6. The natamycin composition of any one of embodiments 1 to 5, wherein the natamycin composition further comprises cellular matter.

Embodiment 7. A natamycin composition comprising natamycin, or a salt thereof, a structuring agent and a surfactant, wherein the natamycin composition further comprises cellular matter.

Embodiment 8. The natamycin composition of any one of embodiments 1 to 7, wherein the natamycin composition is produced by fermenting biomass by a fermentation organism.

Embodiment 9. The natamycin composition of any one of embodiments 6 to 8, wherein the cellular matter comprises remnants of the fermentation organism; compounds excreted by the fermentation organism; remnants of fermentation broth; or a combination thereof.

Embodiment 10. The natamycin composition of any one of embodiments 1 to 9, wherein the natamycin composition has an average particle size of about 6 µm or less.

Embodiment 11. The natamycin composition of any one of embodiments 1 to 10, wherein the composition further comprises at least one wetting agent, or at least one dispersing agent, or a combination thereof.

Embodiment 12. A fungicide, comprising a natamycin composition of any one of embodiments 1 to 8.

Embodiment 13. The fungicide of embodiment 12, further comprising at least one antifoaming agent, at least one thickening agent, at least one stabilizing agent, or glycerol, or any combinations thereof.

Embodiment 14. A method, comprising contacting a plant or a fungus, or a part thereof, with a natamycin composition of any one of embodiments 1 to 11 to treat the plant or fungus, or a part thereof.

Embodiment 15. A method, comprising treating seeds with a natamycin composition of any one of embodiments 1 to 11 to produce treated seeds; and germinating the treated seeds.

Embodiment 16. A method, comprising contacting fruit with a natamycin composition of any one of embodiments 1 to 11.

Embodiment 17. A method, comprising contacting soil with a natamycin composition of any one of embodiments 1 to 11.

Embodiment 18. A method, comprising contacting a crop with a natamycin composition of any one of embodiments 1 to 11.

The invention will now be illustrated by the following examples, which are provided by way of illustration and not of limitation and it will be understood that many variations in the methods.

EXAMPLES

The following Examples are merely illustrative and are not meant to limit any aspects of the present disclosure in any way.

Example 1

Preparation and Formulation of Natamycin Composition

This example describes the preparation and formulation a natamycin composition made up of about 60% natamycin and 40% of other compounds from a fermentation broth of *Streptomyces natalensis*.

A fermentation using *Streptomyces natalensis* was performed. After termination of the fermentation, a natamycin composition was recovered. In particular, the fermentation broth was filtered; the filtration cake was treated with methanol and extracted with 20% NaOH at a pH of about 9-10. After two additional filtration and elution steps, the pH was adjusted to about pH 6.5 by adding 15% HCL. The final natamycin content was set at 60% by addition of 20% glucose. The resulting product was dried and then milled. In particular, 250 g of the dry product per liter of water was milled using a bead mill to obtain more homogeneous particles with an average size of about 2 μm.

As used in the examples herein, "Natamycin Composition A" refers to a natamycin composition comprising the components shown in Table 1a below milled to a D50 (mass median diameter) of 2 μm.

TABLE 1a

| Compound | Content (%) |
|---|---|
| Natamycin | 58.5-61.5% |
| Natamycin methylester | 1.5-4% |
| Water content | <8% |
| Fatty Acids | 6-10% |
| Protein | 9.60% |
| Glucose | 20% |
| Starch | 1.20% |

As used in the examples herein, "Control Natamycin" refers to a commercially available natamycin with a purity of 95% or greater milled to a D50 (mass median diameter) of 2 μm.

Natamycin Composition A and Control Natamycin were formulated using the ingredients provided in Table 1b below. Natamycin Composition A according to the following formulation will be referred to as "Formulation 1". Control natamycin according to the following formulation will be referred to as "Control Natamycin Formulation".

TABLE 1b

| Ingredient | g/l | w/w % |
|---|---|---|
| Natamycin composition A | 100 | 9.09 |
| Atlas G 5002-L | 20 | 1.82 |
| MetaSperse 550 S | 8 | 0.73 |
| Glycerol | 252 | 22.9 |
| Rhodorsil 426R | 6 | 0.55 |
| Rhodopol 23 (2% in water) | 77 | 7 |
| Water | 637 | 57.9 |
| Totals | 1100 | 100 |

Natamycin Composition A was formulated to produce Formula 1 according to the following protocol. Glycerol was first added to water and, while stirring, the surfactants Atlas™ G 5002-L (Croda Crop Care, Cowick Hall, DN14 9AA, UK) and MetaSperse™ 550 S (Croda Crop Care, Cowick Hall, DN14 9AA, UK) were added. After stirring for 30 minutes, 4.8 g of the antifoaming agent Rhodorsil® 426R (Rhodia Inc., Cranbury, N.J.) was added. Natamycin Composition A and Control Natamycin added portion-wise and the suspension was stirred for an additional 30 minutes. The suspension was milled to an average particle size of about 1.7 μm. The suspension was collected and the remaining ⅕ part of Rhodorsil® 426R was added. After stirring for 30 minutes the viscosity modifier Rhodopol® 23 (Rhodia Inc., Cranbury, N.J.) was added. After stirring for an additional 3 hours, the formulations were obtained. A preservative, acticide was added at 50 ppm. Control Natamycin was also formulated using the protocol set forth above to produce Control Natamycin Formulation.

Example 2

Physical and Chemical Characterization of Natamycin Composition A

Various physical and chemical properties were determined for Natamycin Composition A, and compared with the physical and chemical properties of Control Natamycin. Both samples were analyzed by powder X-ray diffraction (PXRD), scanning electron microscopy (SEM), Brunauer-Emmett-Teller theory (BET), and differential scanning calorimetry (DSC). Solubility was also determined for Natamycin Composition A and Control Natamycin.

Powder X-Ray Diffraction

PXRD was used to evaluate the relative amounts of crystalline material in Natamycin Composition A (Natamycin I in Table 20) and Control Natamycin (Natamycin with batch number 140206 in Table 20). Samples were prepared by shaking a slurry of the material, and taking it up into a 0.5 mm glass capillary. PXRD analysis was performed on a diffractometer using CuKα radiation with a fine-focus sealed tube source in capillary mode. A diffractogram of each sample was then obtained in capillary mode. The PXRD data collected from Natamycin Composition A in water (150 gram natamycin) and Control Natamycin in water (250 gram natamycin) are shown in FIG. 2.

Scanning Electron Microscopy (SEM)

SEM images were also obtained for samples of Natamycin Composition A and Control Natamycin, as shown in FIGS. 1A and 1B, respectively.

Saturation Studies

Saturation studies were performed on Natamycin Composition A and Control Natamycin, both at 25% (w/w %) suspension in water. The dissolution medium was prepared by stirring demineralized water and 5% polysorbate 80 (a surfactant) at ambient temperature (22° C.). To prepare the samples for solubility analysis, a plastic pipet was used to add 3 drops (0.25 mL) of thoroughly shaken formulation to 10 mL of the dissolution medium. After 20, 60 and 300 seconds, a 1 ml aliquot was removed from the sample and filtered over a 0.45 μm GHP-filter. Then, 0.05 mL of the mobile phase was added to 0.25 mL of the filtrated natamycin aliquot. The aliquots were then injected individually onto a high performance liquid chromatography (HPLC) column and the resulting peak areas were calculated. The peak areas and ratios are summarized in Table 2 below.

TABLE 2

HPLC peak areas (mAUs) and ratios for the dissolution of Control Natamycin and Natamycin Composition A.

| Time (s) | Control Natamycin | Natamycin Composition A | Ratio (Natamycin Composition A: Control Natamycin) |
|---|---|---|---|
| 20 | 3966 | 8075 | 2.0 |
| 60 | 4077 | 8528 | 2.1 |
| 300 | 4005 | 9266 | 2.3 |

HPLC was performed using a reverse phase column (column dimensions: 4.6×250 mm, 5 μm) with an acetonitrile:phosphaste buffer pH 5.8 mobile phase (ratio 28:72; phosphate buffer=0.7 g/L $Na_2HPO_4*2H_2O$+6.39 g/L $NaH_2PO_4*H_2O$)), a flow rate of 1.0 mL/min, and an injection volume of 5 μL. The column temperature was set to 25° C. and the natamycin was detected at a wavelength of 304 nm.

A higher solubility of Natamycin Composition A was unexpectedly observed, in view of the fact that Natamycin Composition A was observed to have a lower surface area ($m^2/g$) than Control Natamycin, as discussed in further detail below (see BET analysis).

To further demonstrate that Natamycin Composition A results in an increase in natamycin solubility, the liquid phase concentration of natamycin was determined for both Natamycin Composition A and Control Natamycin. To determine the absolute concentration (μg/mL) of natamycin in the liquid phase for each suspension, the suspensions were thoroughly shaken and transferred into individual 2.0 mL centrifuge tubes. The slurries were then centrifuged for 45 min at a rate of 14,500 rpm. The supernatants were then collected and diluted 10-fold with an acetonitrile:water (3:7) solution. The concentration of natamycin in the liquid layer was then determined by injecting the samples individually onto an HPLC and comparing the UV-Vis absorption to that of a standard natamycin stock solution.

The results of this experiment are summarized in Table 3 below and are consistent with solubility studies described above. The amount of dissolved natamycin in Natamycin Composition A was unexpectedly observed to be 2-3 times greater than in Control Natamycin.

TABLE 3

| Sample | Natamycin (μg/mL) |
|---|---|
| Control Natamycin | 68 |
| Natamycin Composition A | 202 |

BET Analysis

Brunauer, Emmett, and Tellers (BET) analysis theory was used to determine the surface area (expressed as $m^2/g$) for Natamycin Composition A and Control Natamycin. Each sample was milled to a particle size of 2 μM prior to BET analysis. The results of analysis for several trials of Composition A and Control Natamycin are shown in Table 4 below.

TABLE 4

| Sample | BET analysis ($m^2/g$) |
|---|---|
| Natamycin Composition A, comprising natamycin batch # 140428 | 1.6 |
| Natamycin Composition A, comprising natamycin batch # 151201 | 3 |
| Natamycin Composition A, comprising natamycin batch # 150820 | 3.6 |
| Control Natamycin, comprising natamycin F | 9.4 |
| Control Natamycin, comprising natamycin batch # 140206 | 7.7 |

Greater BET values generally indicate the presence of more pores and thus more surface area. As seen from the data of Table 4, Natamycin Composition A was unexpectedly observed to have lower surface area per unit mass than Control Natamycin. Specifically, Natamycin Composition A was observed to have an average BET surface area of 2.7 $m^2/g$, while Control Natamycin was observed to have an average BET surface area of 8.5 $m^2/g$.

Differential Scanning Calorimetry

Figure 3:
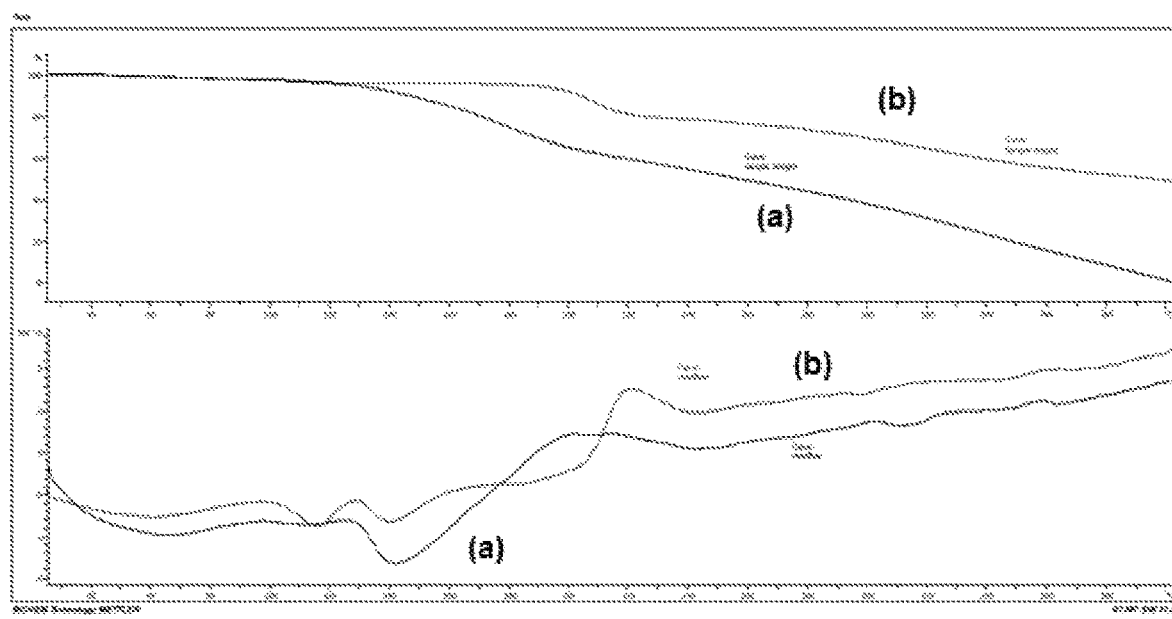
FIG. 3 depicts the DSC thermograms of (top panel) describes the mass that remains (thermogravimetric) and (below panel) showing the heat flow, depicts both (a) Natamycin Composition A and (b) Control Natamycin in water.

Differential scanning calorimetry (DSC) was performed to study the thermal transitions of Natamycin Composition A and Control Natamycin. Analyses were carried out at a heating rate of 10° C./min over a temperature range of 25-400° C. under a nitrogen atmosphere. See FIG. 3. The decomposition of Natamycin Composition A was observed to occur at lower temperature than decomposition of Control Natamycin.

Example 3

Effect on Development of Wheat Seedlings

This example demonstrates the effect of Natamycin Composition A (Natamycin I in Table 20) on the germination of naturally infected wheat seeds and the development and health of the seedlings in a greenhouse.

Wheat seeds were naturally infested with a cocktail of fungi, 18% *Fusarium* spp. and 64% *Microdochium* spp. Formulation 1 was compared to Control Natamycin Formulation (Natamyin F in Table 20), a commercial control Celest® (seed treatment fungicide with fludioxonil as active ingredient, Syngenta), and an untreated control.

Formulation 1 and Control Natamycin Formulation were used at dosages of 0.5, 1 and 2 g Natamycin composition A/kg of seed and 0.5, 1 and 2 g Control Natamycin/kg of seed. The commercial control was used at a dose rate of 0.2 mL/kg of seed. The seeds were treated and sowed in trays and put in a greenhouse following a randomized block system. On day 15, percentage healthy and unhealthy plants were measured. The results are summarized in Table 5 below.

TABLE 5

| Treatment | % healthy seedlings | % unhealthy seedlings |
| --- | --- | --- |
| Untreated | 4 | 28 |
| Celest net 0.2 ml/kg of seed | 38 | 34 |
| Control Natamycin Formulation (2 g of Control Natamycin/kg of seed) | 74 | 22 |
| Formulation 1 (2 g of Natamycin Composition A/kg of seed) | 74 | 18 |
| Control Natamycin Formulation (1 g of Control Natamycin/kg of seed) | 58 | 34 |
| Formulation 1 (1 g of Natamycin Composition A/kg of seed) | 66 | 24 |
| Control Natamycin Formulation (0.5 g of Control Natamycin/kg of seed) | 42 | 40 |
| Formulation 1 (0.5 g of Natamycin Composition A/kg of seed) | 40 | 34 |

As compared to Control Natamycin Formulation, seeds treated with Formulation 1 were unexpectedly observed to yield a similar number of healthy plants and unhealthy plants. These results were surprising since Formulation 1 contains about 60% natamycin, while Control Natamycin Formulation contains about 95% natamycin.

Formulation 1 was also observed to outperform the commercial control for the 2 and 1 g/kg dosage, as 1.9 and 1.7 times more healthy seedlings were observed, respectively.

At the same dosages, Formulation 1 also outperformed the untreated control for the 2 and 1 g/kg dosage, as 18.5 and 14.5 times more healthy seedlings were observed, respectively.

Example 4

Effect on Development of Wheat Seedlings

This example demonstrates the effect of Natamycin Composition A (Natamycin I in Table 20) on the germination of naturally infected wheat seeds and the development and health of the seedlings in a greenhouse.

Wheat seeds were naturally infested with a cocktail of fungi, 60% *Fusarium* spp. and 23% *Microdochium* spp. Formulation 1 was compared to two commercial controls, and an untreated control. The two commercial controls were: Celest® (as described in Example 3 above), and Redigo® (seed treatment fungicide with prothioconazole as active ingredient, Bayer Crop Science).

Formulation 1 was used at dosages of 0.5 and 1 g Natamycin Composition A/kg of seed. Celest® was used at a dose rate of 0.2 ml/kg of seed, and Redigo® at a dose rate of 0.1 ml/kg of seed.

Wheat seeds (4×50 seeds per treatment) were treated with the seed treatment. The seeds were sowed in trays and put in a greenhouse following a randomized block system. On day 15, the percentage healthy and unhealthy plants were measured. The results are summarized in Table 6 below.

TABLE 6

| Treatment | % healthy seedlings | % unhealthy seedlings |
| --- | --- | --- |
| Untreated | 4 | 78 |
| Celest net 0.2 mL/kg of seed | 74 | 20 |

TABLE 6-continued

| Treatment | % healthy seedlings | % unhealthy seedlings |
| --- | --- | --- |
| Redigo 0.1 ml/kg of seed | 26 | 68 |
| Formulation 1 (1 g of Natamycin Composition A/kg of seed) | 72 | 20 |
| Formulation I (0.5 g of Natamycin Composition A/kg of seed) | 78 | 18 |

Treatments with Formulation 1 and Celest result in a comparable number of healthy plants. Further, treatment with Formulation 1 resulted in 2.8 times more healthy seedlings than with Regido® label concentration. Compared to the untreated control, seeds treated with Formulation 1 resulted in 18 times more healthy seedlings.

Example 5

Effect on Development of Wheat Seedlings

This example demonstrates the effect of Natamycin Composition A (Natamycin I in Table 20) on the germination of naturally infected wheat seeds and the development and health of the seedlings in a greenhouse.

Wheat seeds were naturally infested with a cocktail of fungi, 18% *Fusarium* spp. and 64% *Microdochium* spp. Formulation 1 was compared to a commercial control Celest® (as described in Example 3 above).

Formulation 1 was used at dosages of 0.4, 0.2 and 0.1 g Natamycin Composition A/kg of seed. Celest® was used at a dose rate of 0.2 mL/kg of seed. The seeds were treated and sowed in trays and put in a greenhouse following a randomized block system. On day 15, the percentage healthy and unhealthy plants were measured. The results are presented in Table 7 below.

TABLE 7

| Treatment | % healthy seedlings | % unhealthy seedlings |
| --- | --- | --- |
| Untreated | 12 | 80 |
| Celest net 0.2 mL/kg of seed | 78 | 16 |
| Formulation 1 (0.4 g of Natamycin Composition A/kg of seed) | 80 | 16 |
| Formulation 1 (0.2 g of Natamycin Composition A/kg of seed) | 64 | 32 |
| Formulation 1 (0.1 g of Natamycin Composition A/kg of seed) | 46 | 50 |

Seeds treated with Formulation 1 at 0.4 g of Natamycin Composition A/kg of seed developed into a similar number of healthy plants and unhealthy plants as compared to the commercial control.

Example 6

Effect on Development of Wheat Seedlings

This example demonstrates the effect of Natamycin Composition A (Natamycin I in Table 20) on the germination of naturally infected wheat seeds and the development and health of the seedlings in the field.

Wheat seeds were naturally infested with a cocktail of fungi, 60% *Fusarium* spp. and 23% *Microdochium* spp. Formulation 1 was compared to two commercial controls: Celest® and Redigo® (as described in Examples 3 and 4 above).

Formulation 1 was used at dosages of 1 and 0.5 g Natamycin Composition A/kg of seed. Celest® was used at a dose rate of 0.2 ml/kg of seed, and Redigo® at a dose rate of 0.1 ml/kg of seed.

The seeds were treated and sowed in the field with 4 replicates per treatment in plots of 20 m$^2$. After 2.5 months, the plants per m$^2$ per treatment were counted. At the end of the season, the wheat was harvested and yield was determined in weight for each treatment. The results are presented in Table 8.

TABLE 8

| Treatment | Plants per m$^2$ | Yield (Q/ha) |
|---|---|---|
| Untreated | 108 | 78.7 |
| Celest net 0.2 ml/kg of seed | 178 | 86.6 |
| Redigo 0.1 ml/kg of seed | 220 | 85.5 |
| Formulation 1(1 g of Natamycin Composition A/kg of seed) | 214 | 88.1 |
| Formulation 1 (0.5 g of Natamycin Composition A/kg of seed) | 206 | 88.7 |

Formulation 1 was observed to have comparable efficacy to Redigo® at all dosages tested. Formulation 1 was also observed to outperform Celest®, and treatment with Formulation 1 also resulted in twice as many plants as the untreated control. Treatment with Formulation 1, Redigo, or Celeste at all dosages tested resulted in comparable yields of wheat (Q/ha), but treatment with Formulation 1 resulted in a yield that was 1.1 times higher than the untreated control.

Example 7

Effect on Development of Corn Seedlings

This example demonstrates the effect of Natamycin Composition A (Natamycin I in Table 20) on the development of corn seedlings.

Formulation 1 and Control Natamycin Formulation ((Natamycin F in Table 20) were applied to corn seeds (150 seeds per treatment). The dosages are listed in Table 9 below. A set of untreated control seeds were also included in the study. Following treatment, the seeds were incubated using a cold test protocol that simulates the unfavorable cold and wet weather conditions that may occur during the planting season. The results of this test are used to predict performance a seed lot will under similar conditions in the field. To perform the test, the seeds were first packed in rolls with saturated field earth and paper towels, then the rolls were placed in plastic bags. The seeds were turned so that the side of the kernel closest to the embryo was down against the soil. The source of the field earth was a plot where corn was previously grown and the soil was known to contain a high number of unidentified mold species. After an incubation period under cold conditions (7 days at 8° C. in the dark followed by 7 days at 25° C. in the light) the number of normal seedlings, abnormal seedlings, and dead seeds were recorded. The results are summarized in Table 9 below. Over the course of the experiment, no phytotoxicity resulting from the natamycin treatment was observed.

Table 9

TABLE 9

| Treatment | % healthy plants | % abnormal plants | % dead seeds |
|---|---|---|---|
| Untreated | 0 | 2 | 98 |
| Control Natamycin Formulation (0.25 g Control Natamycin/ kg of seed) | 11 | 4 | 85 |
| Formulation 1 (0.25 g Natamycin Composition A/kg of seed) | 14 | 13 | 73 |
| Control Natamycin Formulation (0.5 g Control Natamycin/kg of seed) | 12 | 7 | 81 |
| Formulation 1 (0.5 g Natamycin Composition A (/kg of seed) | 20 | 12 | 68 |

The number of healthy seedlings observed was unexpectedly greater when Formulation 1 was applied compared to Control Natamycin Formulation. In particular, dosages of Natamycin Composition A at 0.25 g/kg of seed and 0.5 g/kg of seed resulted in 1.3 and 1.7 times more in the number of healthy plants, respectively, than the identical dosage of Control Natamycin.

Example 8

Effect on Development of Mushrooms

This example demonstrates the effect of Natamycin Composition A (Natamycin I in Table 20) on the development and yield of mushrooms.

Contaminated Phase III compost inoculated with mushroom spawn of the edible mushroom species, Agaricus bisporus, was obtained. Boxes were filled with the compost and incubated for 4 days at a temperature of 21° C. in the dark to allow the mycelium to grow to the surface of the box. After the incubation period, a white mushroom mycelium was visible on the surface of the compost. The compost was then covered with 3 cm of casing. Then, 30 ml of either Formulation 1 or Control Natamycin Formulation (Natamycin F in Table 20) was sprayed onto the casings to give final concentration of 0.4 gram/m$^2$. Each experimental treatment composition was replicated eight times and the untreated control was replicated five times. Following treatment, the boxes were further incubated in the dark at a temperature of 18° C. During the test, dehydration of the casing surface was prevented by spraying sufficient and equal amounts of water (~10 mL) onto the casing of each box every few days. To stimulate mushroom formation, an additional 100 mL of water was added to each box on the 14th and 21st days of incubation. Over a period of 30 days, the mushrooms were harvested daily and total yield was determined by measuring the weight of the mushrooms. The total yield and the yield increase of mushrooms for each treatment after 30 days of incubation are summarized in Table 10. Untreated control was control set to 0%.

TABLE 10

| Treatment | Average yield (grams) | Yield increase (%) |
|---|---|---|
| Control | 141 (n = 5) | 0 |
| Control Natamycin Formulation | 186 (n = 8) | +32% |
| Formulation 1 | 194 (n = 8) | +38% |

Formulation 1 was unexpectedly observed to enhance the yield increase by 6% as compared to Control Natamycin Formulation.

Example 9

Effect on Development of Citrus Fruit

This example demonstrates the effect of Natamycin Composition A (Natamycin I in Table 20) on the development of a citrus fruit, oranges.

Formulation 1 and Control Natamycin Formulation (Natamycin F in Table 20) were used to determine the efficacy against fungal disease on Valencia oranges, as compared to a commercial control and an untreated control. The commercial control was FRUITGARD® M (fungicide with 45% thiophanate-methyl as active ingredient, Fruitgard LLC).

A spore suspension of the orange spoilage mold, *Penicillium* digitatum, was prepared using well-known methods. The oranges were then inoculated with the spore suspension at a concentration of 10.000 spores/mL by the immersion method and the treatments were applied on the oranges using a pilot drencher. For each treatment, 333 oranges divided over 2 boxes (166 and 167 oranges) were used. The concentration of the treatments was 1000 ppm, resulting in about 1 mg of treatment/dm$^2$ of orange peel. The commercial control was used at a dosage of 0.3 grams active ingredient/unit. Following treatment, the oranges were stored at room temperature. After 15 days, the number of molded oranges was determined and the percentage of molded oranges was calculated. The results are summarized in Table 11 below.

TABLE 11

| Treatment | Total # of molded oranges | Average % molded oranges |
|---|---|---|
| Untreated | 91 | 27.3 |
| Control Natamycin Formulation (1000 ppm) | 54 | 16.2 |
| Formulation 1 (1000 ppm) | 44 | 13.2 |
| FRUITGARD ® M (0.3 g AI/unit) | 50 | 15.0 |

*AI = active ingredient

Even under challenging growth conditions, treatment of oranges with Formulation 1 resulted in a lower number of molded fruits (44 oranges) than the untreated control. The results of Formulation 1 were observed to be similar to the results obtained for Control Natamycin Formulation, where 54 molded fruits were found at the end of the study. These results were unexpected because Formulation 1 contained a lower percentage of the active ingredient than Control Natamycin Formulation, yet their efficacy was comparable. The results from this study also demonstrate that treatment with Formulation 1 resulted in a similar number of molded oranges (54 molded oranges) than the commercial control (50 molded oranges).

The results from this experiment demonstrated that the Formulation 1 and the Control Natamycin Formulation both performed better than the untreated control and had similar efficacy, despite the fact that the Formulation 1 had a much lower content of actual natamycin compared to Control Natamycin Formulation (60% compared to 95%). Both treatments also performed similarly at dosages of 500 ppm and 1000 ppm to the commercial product FRUITGARD®.

Example 10

Effect on Soybeans Against *Fusarium Graminearum*

This example demonstrates the effect of Natamycin Composition A (Natamycin I in Table 20) on soybeans inoculated with *Fusarium graminearum*.

The trials were conducted inside a greenhouse. The weather conditions during the trial period were cooler than usual, but the greenhouse temperature was set to 85° F. for the duration of the experiment.

The study was performed as a 13-treatment, six-replication trial. A total of 104 seeded cells were used for every tray, and each tray represented one replication for each treatment. The replications for each treatment were blocked close together to facilitate evaluations. The trays received water twice daily until emergence, then water was reduced to once a day. Prior to seeding, the soil mix was inoculated with *Fusarium graminearum* one day before planting, at a dosage of 1 part of inoculum to 10 parts of soil. The trays were then filled with soil and seeded by hand (one seed per cell) on week 1 and the seeds emerged on week 2. There were 13 different treatments in this study, including a commercial control—Maxim® 4 FS (seed treatment fungicide, Syngenta), an untreated control, Control Natamycin Formulation (Natamycin F in Table 20) and Formulation 1, comprising Natamycin Composition A (Natamycin I in Table 20). Each of the treatments were tested at several concentrations.

Two evaluations were made in this study to evaluate the effectiveness of Natamycin Composition A; stand count and vigor. Evaluations of each plot were performed 9, 12, 16, 22, 29 and 35 days after planting. On the day of the evaluations, every seedling on each tray was counted and the whole tray was visually evaluated for vigor on a 0-10 scale. The results are presented in Table 12 below.

TABLE 12

| Treatment * | Average Vigor | Number of plants at last count | Plant loss (%) |
|---|---|---|---|
| Maxim 4 FS 1.25 g AI/100 kg | 8.4 | 89 | 6 c |
| Maxim 4 FS 2.5 g AI/100 kg | 6.6 | 79 | 12 c |
| Maxim 4 FS 5 g AI/100 kg | 7.5 | 79 | 17 bc |
| Maxim 4 FS 10 g AI/100 kg | 7.4 | 65 | 32 abc |
| Natamycin Composition A 2.5 g AI/100 kg | 7.9 | 77 | 19 bc |
| Natamycin Composition A 5 g AI/100 kg | 8.5 | 73 | 23 bc |
| Natamycin Composition A 10 g AI/100 kg | 8.1 | 72 | 24 bc |
| Natamycin Composition A 20 g AI/100 kg | 7.8 | 47 | 50 ab |
| Control Natamycin 2.5 g AI/100 kg | 7.9 | 47 | 52 ab |
| Control Natamycin 5 g AI/100 kg | 7.8 | 45 | 52 ab |
| Control Natamycin 10 g AI/100 kg | 7.5 | 36 | 62 a |
| Control Natamycin 20 g AI/100 kg | 7.7 | 45 | 52 ab |
| Untreated control | 7.4 | 35 | 63 a |

AI = Active Ingredient
* Natamycin A and Control Natamycin were formulated as indicated in Example 1.

All the formulations tested provided some level of control of *Fusarium graminearum* when compared to the untreated controls. The results of this example further demonstrate that plant loss varied drastically between different treatments. Untreated control trays and trays treated with the Control Natamycin Formulation suffered the highest number of plant losses (up to 65%) and show a low average vigor while Formulation 1 and commercial control showed lowest number of plant loss and a high average vigor.

Natamycin composition A displayed similar disease control at their lowest dosages (1.25 g AI/100 kg and 2.5 g AI/100 kg, respectively) when compared to the Commercial control. Natamycin composition A unexpectedly performed better than Control Natamycin.

Example 11

Banana Post-Harvest Treatment for Protection Against Crown Rot Mold

Crown rot is a post-harvest disease for bananas that may be caused by different mold species, including, for example, *Colletotrichum musae, Fusarium pallidoroseum* and *Fusarium proliferatum*. This example demonstrates the effect of Natamycin Composition A (Natamycin I in Table 20) on crown rot mold on bananas.

Exportation banana boxes of 18.14 kg at ripening stage 1 were used. The bananas did not receive any fungicide treatments at the packing station. All bananas were inoculated with a mixture of crown rot pathogens ($10^5$ conidia/mL) and the treatments were applied two hours after the inoculation. The treatments were applied as mixture containing water and Alumbre $NH_4Al(SO_4)_2 \cdot 12H_2O$ (2%) that was diluted the day before. The treatments were then applied with an airbrush, and each treatment was done on one box of bananas. The list of evaluated treatments is listed in Table 13 below. A-non inoculated treatment was also included to determine the natural inoculum pressure of the farm. Following application of the treatment, the bananas were stored in a refrigerated room at 14° C. for 14 days. After this time period elapsed, the temperature was raised to 17° C. to pre-cool the bananas prior to ripening. After stabilization of temperature, ethylene was introduced at a concentration of 100-150 ppm for 24 h. Five days after induction (ethylene treatment), the bananas had reached ripening stage 5-6 and the banana evaluations were performed.

TABLE 13

| Treatment and Dosage (ppm)* | Active ingredient |
|---|---|
| Formulation 1 (250 ppm) | Natamycin Composition A |
| Formulation 1 (500 ppm) | Natamycin Composition A |
| Control Natamycin Formulation (250 ppm) (Natamycin F in Table 20) | Control Natamycin |
| Control Natamycin Formulation (500 ppm) (Natamycin F in Table 20) | Control Natamycin |
| Formulation 1 (500 ppm) + Mertect 22 SL (500 ppm) | Natamycin Composition A + Thiabendazole |
| ControlNatamycin Formulation (500 ppm) + Mertect 22 SL (500 ppm) | Control Natamycin + Thiabendazole |
| Formulation 1 (500 ppm) + Magnate 75 SG (750 ppm) | Natamycin Composition A + Imazalil |
| Control Natamycin Formulation (500 ppm) + Magnate 75 SG (750 ppm) | Control Natamycin + Imazalil |
| Magnate 75 SG (750 ppm) + Mertect 22 SL (500 ppm) | Imazalil + Thiabendazole |
| Bankit 250 SC (250 ppm) + Mertect 22 SL (500 ppm) | Azoxistrobin + Thiabendazole |
| Untreated fruit—inoculated | — |
| Untreated fruit—non inoculated | — |

*Natamycin A and Control Natamycin were formulated as indicated in Example 1.

Disease incidence and severity were assessed for each cluster. A cluster was considered infected if any lesions were observed regardless of size. The bananas were then sorted into various groups with respect to the severity of the observed crown rot infection: (1) banana clusters with completely healthy crowns, (2) banana clusters with crown rot lesions where less than 25% area affected, (3) banana clusters with crown lesions where between 25-50% of the area was affected, and (4) banana clusters with crown rot lesions where more than 50% of the area was affected. The results of the bananas evaluations for disease incidence and severity are summarized in Table 14.

TABLE 14

| Treatment | Disease incidence (%) and TUKEY Test Group | No symptoms (%) | Disease severity (%) <25% | 25-50% | >50% |
|---|---|---|---|---|---|
| 1Formulation 1 250 ppm | 11.7 AB | 88.3 | 0 | 0 | 11.7 |
| 2. Formulation 1 500 ppm | 11.0 AB | 89.0 | 11 | 0 | 0 |
| 3. Control Natamycin Formulation 250 ppm | 6.2 A | 93.8 | 0 | 0 | 6.2 |
| 4. Control Natamycin Formulation 500 ppm | 17.6 AB | 82.4 | 6.0 | 0 | 11.6 |
| 5. Formulation 1 500 ppm + TBZ 500 | 5.2 A | 94.8 | 0 | 0 | 5.2 |
| 6. Control Natamycin Formulation 500 ppm + TBZ 500 | 11.8 AB | 88.2 | 0 | 0 | 11.8 |
| 7. Formulation 1 500 ppm + IZL 750 | 0.0 A | 100.0 | 0 | 0 | 0 |
| 8. Control Natamycin Formulation 500 ppm + IZL 750 | 11.0 AB | 89.0 | 0 | 0 | 11.0 |
| 9. IZL 750 + TBZ 500 | 0.0 A | 100.0 | 0 | 0 | 0 |
| 10. AZT 250 + TBZ 500 | 0.0 A | 100.0 | 0 | 0 | 0 |
| 11. Untreated fruit—inoculated | 86.0 B | 14.0 | 0 | 7.0 | 79.0 |
| 12. Untreated fruit—non inoculated | 0.0 A | 100.0 | 0 | 0 | 0 |

TBZ = Thiabendazole
IZL = Imazalil
AZT = Azoxistrobin

A multiple comparison test (Tukey test) for the disease incidence parameter was performed using INFOSTAT statistical analysis. Letters in columns 2 refer to the Tukey test; individual entries followed by an identical series of letters are not statistically different from one another (P=0.05). The results for the disease incidence (%) and statistical analysis for crown rot symptoms are summarized in Table 14 above.

For each dosage tested, Formulation 1 and Control Natamycin Formulation had comparable efficacy. These results were unexpected because Formulation 1 contains a lower percentage of the active ingredient than Control Natamycin Formulation. Despite the fact that the Formulation 1 had a much lower content of actual natamycin compared to Control Natamycin Formulation (60% compared to 95%), their efficacy was comparable.

Additionally, when Formulation 1 was combined with other fungicides, Formulation 1 unexpectedly performed better than Control Natamycin Formulation. Formulation 1 (500 ppm) used in combination with IZL (750 ppm) (Table 14, entry 7) was unexpectedly observed to have the highest efficacy among all treatments tested.

Example 12

Effect on Bananas Against *Mycosphaerella Fijiensis*

This example demonstrates the efficacy of Natamycin Composition A (Natamycin I in Table 20) for the control of *Mycosphaerella fijiensis*.

An experimental unit had 9 banana plants that were planted in plots with 3 m between plants. The trial followed a complete randomized design and each treatment was replicated three times. Border rows between the treated plants were planted with *Musa textilis*, a variety of banana plant tolerant to black Sigatoka. All treatments were applied using a motor blower to give a total treatment volume of 23 L/ha. The tested treatments were applied as an oil-water emulsion using Spraytex® oil (5 L/ha) and 1% Imbirex emulsifier. The tested fungicide treatments are listed in Table 15 below, along with their respective active ingredient(s) and dilution (or concentration). The last application of the experimental test treatment was performed on 13 weeks after the first application. A total of 16 consecutive applications were performed over the course of the study.

TABLE 15

| Treatment* | Active Ingredient | Dilution or l/ha |
|---|---|---|
| 1. Control Natamycin Formulation (Natamycin F in Table 20) + Dithane 1.0 l/ha | Control Natamycin + mancozeb | 100 X |
| 2. Formulation 1 + Dithane 1.0 l/ha | Natamycin Composition A + mancozeb | 100 X |
| 3. Control Natamycin Formulation (Natamycin F in Table 20) + Dithane 0.5 l/ha | Control Natamycin + mancozeb | 100 X |
| 4. Formulation 1 + Dithane 0.5 l/ha | Natamycin Composition A + mancozeb | 100 X |
| 5. Control Natamycin Formulation (Natamycin F in Table 20) ** | Control Natamycin | 50 X |
| 6. Dithane 0.5 l/ha | Mancozeb | 0.5 l/ha |
| 7. Dithane 1.0 l/ha | Mancozeb | 1.0 l/ha |
| 8. Dithane 2.0 l/ha | Mancozeb | 2.0 l/ha |
| 9. Mineral oil | Mineral oil—Spraytex ® | 5.0 l/ha |
| 10. Untreated plants | — | |

*Formulations used were as indicated in Example 1.
** Control Natamycin Formulation was provided as a suspoemulsion including oil The following variables were evaluated every week for each of the treatments: total leaves per plant, youngest leaf with streaks (i.e., youngest leaf infected (YLI)), youngest leaf with spots (YLS) and disease severity. The first appearance of symptoms in banana leafs correlated with the severity of the infection: the lower the leaf number in which the symptoms appear, the higher the level of infection. Disease evaluations were conducted once the first applied leaf reached position #4 and every 7 days henceforth until one week after the final treatment application. Note that Position 4 is leaf 4. The treatment response to black Sigatoka was evaluated using the Stover scale modified by Gauhl (Table 16 below) and the results of the evaluations are shown in Table 17 below.

TABLE 16

Stover scale modified by Gauhl used to determine disease grade

| Grade | Description |
|---|---|
| 0 | No symptoms of the disease |
| 1 | Streaks to a maximum of 10 spots |
| 2 | 11 spots to 5% of the leaf area |
| 3 | 6-15% |
| 4 | 16-33% |
| 5 | 34-50% |
| 6 | More than 50% |

TABLE 17

| Treatment | Average YLI | Average YLS | Average Number of leaves | Average Severity |
|---|---|---|---|---|
| 1. Control Natamycin Formulation + Dithane 1.0 l/ha | 4.7 | 5.4 | 6.6 | 0.71 |
| 2. Formulation 1 + Dithane 1.0 l/ha | 4.7 | 5.4 | 6.9 | 0.74 |
| 3. Control Natamycin Formulation + Dithane 0.5 l/ha | 4.4 | 5.0 | 6.5 | 0.86 |
| 4. Formulation 1 + Dithane 0.5 l/ha | 4.6 | 5.3 | 7.3 | 0.85 |
| 5. Control Natamycin Formulation* | 4.1 | 4.7 | 7.2 | 1.40 |
| 6. Dithane 0.5 l/ha | 4.6 | 5.3 | 7.4 | 0.95 |
| 7. Dithane 1.0 l/ha | 4.9 | 5.7 | 7.0 | 0.63 |
| 8. Dithane 2.0 l/ha | 4.8 | 5.6 | 7.1 | 0.60 |
| 9. Mineral oil | 4.2 | 4.9 | 7.3 | 1.35 |
| 10. Untreated plants | 3.3 | 4.3 | 7.4 | 2.17 |

*Control Natamycin Formulation was provided as a suspoemulsion including oil

With the exception of the oil treatments (Table 17, entry 5 and 8) all treatments had a severity below 1 while the untreated plant had a severity above 2. All treated plants have an average YLI between the 4 and 5 while the untreated plant has an average YLI of 3.3. Both conclusions indicate that all treatments had a fungicide effect. These results were unexpected because Formulation 1 contains a lower percentage of the active ingredient than Control Natamycin Formulation, yet their efficacy was comparable. Formulation 1 has the same efficacy against fungi as a commercial product with the active ingredient mancozeb.

Example 13

Effect of Formulation 1 as Soil Application Against *Fusarium*

This example demonstrates the effect of formulated Natamycin Composition A (Formulation 1; Natamycin I in Table 20) as a soil application against *Fusarium* spp. on banana plants.

Formulation 1 and Control Natamycin Formulation (Natamycin F in Table 20) were used to determine the efficacy against fungal disease in a greenhouse trial on banana plantlets. The soil was infested with *Fusarium* spp. following well known methods using a concrete mixer. The infested soil was thoroughly mixed with the various treatments as mentioned in Table 19 below. For some of the treatments Formulation 1 and Control Formulation were coated on sand particles and these sand particles were mixed with the potting soil in the concrete mixer. The infested and treated soil was used to fill-out the pots that were planted with two-month old banana plants. Three repetitions were used for each treatment. 6 weeks after planting the plants were uprooted and cut in half and the internal infestation symptoms on the cut edge were scored based on the scale in Table 18 below.

TABLE 18

| Grade | Description |
|---|---|
| 0 | 0% discoloration |
| 2 | <5% isolated necrotic points |
| 3 | 5-30% necrosis |
| 4 | 31-50% necrosis |

TABLE 18-continued

| Grade | Description |
|---|---|
| 5 | 50-90% necrosis |
| 6 | 90-100% necrosis |

TABLE 19

| Treatment and dosage | Average grade | Significancy test |
|---|---|---|
| Formulation 1 (100 ppm) | 4 | CD |
| Formulation 1 (1000 ppm) | 0.7 | AB |
| Control Natamycin Formulation (100 ppm) | 3.7 | CD |
| Control Natamycin Formulation (1000 ppm) | 0 | A |
| Natamycin Composition A coated on sand (100 ppm) | 4 | CD |
| Natamycin Composition A coated on sand (1000 ppm) | 0 | A |
| Control Natamycin coated on sand (100 ppm) | 3 | BC |
| Control Natamycin coated on sand (1000 ppm) | 0.7 | AB |
| Untreated Fusarium infestation | 5 | D |
| Untreated without Fusarium infestation | 0 | A |

Table 19 shows the average grade based on Table 18 of three replicates of each treatment. The significance was calculated using ANOVA followed by Fisher's protected least significant difference test.

At 1000 ppm, Formulation 1 and Natamycin Composition A coated on sand have similar efficacy against *Fusarium* spp. as Control Natamycin Formulation and all three are similar to plantlets untreated without *Fusarium* spp. infestation. These results were surprising given that Formulation 1 and Natamycin Composition A coated on sand contain with 60% a lower amount of the active ingredient natamycin, while Control Natamycin contains 95% of the active ingredient natamycin.

Example 14

Analysis of Different Batches of Crude and Purified Natamyin

This example shows differences between crude natamycin preparations and purified natamcyin preparations.

Several batches of crude natamcyin, prepared as described herein above, and commercial batches of purified natamycin (95%) were obtained and analysed.

Table 20 denotes some characteristics of these batches.

TABLE 20

Concentration of natamycin, fatty acids (FA), protein and starch in different natamycin batches.

| Natamycin | Batch | Natamycin % (w/w) | Crude (C) or Purified (P) | D0.5 (µm)[1] | BET (m²/g) | FA (% w/w) |
|---|---|---|---|---|---|---|
| Natamycin A | 140428 | 60 | C | 12.9 | 1.14 | 10.1 |
| Natamycin B | 151201 | 60 | C | 13.3 | 2.98 | 2.84 |
| Natamycin C | 150820 | 60 | C | 8.5 | 3.58 | 0.65 |
| Natamycin D | 20160716-32 | 85 | C | 11.5 | 3.3 | 0.05 |
| Natamycin E | 140423 | 95 | P | 14.4 | n.d. | 1.04 |
| Natamycin F | 20150106 | 95 | P | 15.3 | 9.36 | <0.1 |
| Natamycin G | 20160716 | 80 | C | 3.2 | 4.92 | 0.3 |
| Natamycin H | 161010 | 60 | C | n.d | n.d. | 10.2 |
| Natamycin I | 140305 | 60 | C | n.d | 2.8 | 5.86 |
|  | 160915 | 60 | C | 5 | n.d. | 8.6 |
|  | 20161027 | 80 | C | n.d. | n.d. | n.d. |
|  | 161110 | 68 | C | n.d. | n.d. | n.d. |
|  | 140206 | 95 | P | n.d. | 7.73 | n.d. |
|  | 160303 | 60 | C | n.d. | 1.71 | 1.04 |

[1]D0.5 indicates the average particle size of the particles

Example 15

The Effect of Crude Natamycin Compared to Purified Natamycinin

This example demonstrates the enhanced bioavailability and fungicidal effects of crude natamycin.

*Saccharomyces cerevisiae* (at least $10^5$ cfu/ml) was distributed on Petri dishes with a diameter of 145 mm containing 30 ml Potato Dextrose Agar (PDA; Carl Roth; pH of about 6) using sterilized swabs. Filter paper discs (Whatman, Antibiotic Assay Paper, grade AA) with a diameter of 6 mm were loaded with 10 µl of a solution of 3 mM natamycin from different sources.

Following the application of a filter, Petri dishes were incubated for 16 h h in a refrigerator at 4° C. to allow diffusion of natamycin into the agar. After 16 h the filter discs were removed from the agar and the Petri dishes were incubated upside down in a stove at 30° C. The size of the inhibition zone shows the efficacy against yeast of the natamycin released from the filter disc. After 24 h incubation in the stove the size of the inhibition zone was determined using a digital caliper gauge.

The data are presented as square mm and are an average of six replicas. The effect of 3 mM natamycin on yeast growth in Petri dishes was determined as described herein above. Numbers represent surface of inhibition zones expressed in square mm.

TABLE 21

Bioavailability of natamycin

| Treatment | Inhibition zone (mm²) |
|---|---|
| Natamycin H | 405 |
| Natamycin I | 306 |
| 20161027 | 348 |
| Natamycin F | 183 |

Natamycin H, I and sample number 20161027 comprise cellular matter and show a higher inhibition zone compared to Natamycin F which was purified.

Example 16

The Effect of Crude Natamycin Compared to Purified Natamycin

This example demonstrates the enhanced fungicidal effects of crude natamycin.

Same methods as described above in Example 15. The effect of 3 mM natamycin on yeast growth in Petri dishes was determined as described herein above, unless otherwise indicated.

Depicted herein below in Tables 22 and 23 are the results of several independent experiments, all performed in sextuple. Numbers represent average surface of inhibition zones expressed in square mm.

TABLE 22

Bioavailability of natamycin

| Treatment | Inhibition zone (mm²) |
|---|---|
| Natamycin H | 299 |
| 161110 | 279 |
| 160915 | 259 |
| Natamycin A | 286 |
| 140206 | 167 |

Natamycin H and A comprise cellular matter and show a higher inhibition zone compared to Natamycin E which was purified.

Table 23 shows results obtained with method as explained as in Example 15, except that 40 μl of natamycin solution was added to the filter paper discs.

TABLE 23

Bioavailability of natamycin

| Treatment | Inhibition zone (mm2) |
|---|---|
| Natamycin A | 819 |
| Natamycin E | 585 |

Natamycin A comprises cellular matter and shows a higher inhibition zone compared to Natamycin E which was purified.

TABLE 24

Bioavailability of natamycin

| Treatment | Inhibition zone (mm2) |
|---|---|
| 160915 | 407 |
| Natamycin A | 367 |
| Natamycin E | 242 |

Natamycin A and batch 160915 comprise cellular matter and show a higher inhibition zone compared to Natamycin E which was purified.

TABLE 25

Bioavailability of natamycin

| Treatment | Inhibition zone (mm2) |
|---|---|
| Natamycin G | 355 |
| Natamycin D | 295 |
| Natamycin F | 142 |

Natamycin G and D comprise cellular matter and show a higher inhibition zone compared to Natamycin F which was purified. These three natamycin batches were obtained from the same supplier. It is noted that the results with Natamycin D, comprising less than 0.05% (w/w) fatty acids, are similar to the results with Natamycin G, comprising 0.3% (w/w) fatty acids.

TABLE 26

Bioavailability of natamycin

| Treatment | Inhibition zone (mm2) |
|---|---|
| Natamycin A | 311 |
| 160915 | 296 |
| Natamycin E | 188 |

TABLE 27

Bioavailability of natamycin

| Treatment | Inhibition zone (mm2) |
|---|---|
| 160915 | 313 |
| Natamycin A | 338 |
| Natamycin E | 179 |

Natamycin A and B, and batch 160915 comprise cellular matter and show a higher inhibition zone compared to Natamycin E which was purified. These natamycin batches were obtained from the same supplier.

TABLE 28

Bioavailability of natamycin

| Treatment | Inhibition zone (mm2) |
|---|---|
| Natamycin A | 182 |
| Natamycin E | 110 |
| Natamycin H | 246 |

Natamycin A and H comprise cellular matter and show a higher inhibition zone compared to Natamycin E which was purified. These natamycin batches come from the same supplier.

TABLE 29

Bioavailability of natamycin

| Treatment | Inhibition zone (mm2) |
|---|---|
| Natamycin D | 149 |
| Natamycin F | 100 |
| Natamycin G | 207 |

Natamycin G and D comprise cellular matter and show a higher inhibition zone compared to Natamycin F which was purified. These natamycin batches come from the same supplier. It is noted that the results with Natamycin D, comprising less than 0.05% (w/w) fatty acids, are similar to the results with Natamycin G, comprising 0.3% (w/w) fatty acids.

Example 17

The Effect of Natamycin Comprising Cellular Matter Compared to Purified Natamycin This example demonstrates the enhanced fungicidal effects of crude natamycin compositions.

*Saccharomyces cerevisiae* (at least $10^5$ cfu/ml) was distributed on Petri dishes with a diameter of 90 mm containing 10 ml PDA agar (Carl Roth, pH about 6) using sterilized swabs. Filter paper discs (Whatman) with a diameter of 6 mm were loaded with 50 µl of a solution containing a concentration of 3 mM natamycin.

The size of the inhibition zone is a result of the natamycin released from the sample disc. After 24 h of incubation in the stove the size of the inhibition zone was measured using a digital caliper gauge. After measuring, the filter discs were removed and replaced on a new Petri dish similar to the previous one (90 mm containing 10 ml PDA agar and *Saccharomyces cerevisiae* (at least $10^5$ cfu/ml) distributed by swabs). 24 hours after the replacement of the filters, the inhibition zone was measured again. The data are presented as square mm and are an average of four replicas.

TABLE 30

Bioavailability of natamycin

| Treatment | Inhibition zone (mm$^2$) | |
|---|---|---|
| | 24 h | 48 h |
| Natamycin A | 720 | 373 |
| Natamycin E | 480 | 298 |

Natamycin A comprises cellular matter and shows a higher inhibition zone compared to Natamycin E which was purified.

Example 18

Antifungal Effect of Natamycin Comprising Cellular Matter Against *Botrytis* on Apples This example demonstrates the antifungal effect of natamycin compositions comprising cellular matter against *Botrytis* on apple.

Tested fruit: apples cv Elstar from organic origin/SKAL certified. SKAL is a semi-governmental Dutch organization that controls organic production in the Netherlands. Wounds of the apples were checked at day 3. Natamycin with different proteins and starch contents were tested at a natamycin concentration of 100 ppm. The formulations were milled to a particle size as indicated in Table 31.

TABLE 31

| | Batch # | d0.5 (µm) | d0.9 (µm) |
|---|---|---|---|
| Natamycin A | 140428 | 2.5 | 9.8 |
| Natamycin B | 151201 | 4.6 | 16.1 |
| Natamycin D | 20160716-32 | 7.3 | 18.8 |
| Natamycin E | 140423 | 8 | 17.9 |
| Natamycin F | 20150106 | 5.1 | 16.4 |
| Natamycin C | 150820 | 5.4 | 13.5 |

Used pathogen: *Botrytis cinerea* spore-suspension containing $2*10^6$ spores/ml.

Application: The fruit peel of the apple was damaged with a cork borer, ø 4 mm and depth ~0.5 cm into the fruit, with 2 wounds per apple. 40 microliter of a freshly prepared spore suspension of *B. cinerea* was applied by pipette onto each wound. Subsequently, the spore-suspension was allowed to air-dry for 4 hours. Then, 50 microliter of a treatment as presented in the list above was applied by pipette to each wound.

All fruits were kept at room temperature (20° C.). Wounds of the apples were checked after 3 days of incubation. The efficacy was calculated by measuring the surface area (square mm) of the rot on the apples compared to the untreated control (see Tables 31 and 32).

Replicates: All treatments for the apple experiment were performed on six individual apples with two wounds each resulting in 12 wounds per treatment.

Results

The results of these experiments are depicted in Table 32

TABLE 32

| Treatment | Efficacy (%) |
|---|---|
| Natamycin A | 88.1 |
| Natamycin B | 68.6 |
| Natamycin C | 63.7 |
| Natamycin E | 54 |
| Untreated control | 0 |
| Control without fungal infection | 100 |

Natamycin E was purified and shows a lower efficacy on apples compared to Natamycin A, B and C which all comprise cellular matter. These natamycin batches were obtained from the same supplier.

TABLE 33

| Treatment | Efficacy (%) |
|---|---|
| Natamycin D | 68 |
| Natamycin F | 60.2 |
| Untreated control | 0 |
| Control without fungal infection | 100 |

Natamycin F was purified and shows a lower efficacy on apples compared to Natamycin D which comprises cellular matter. These natamycin batches were obtained from the same supplier.

Example 19

Antifungal Effect of Crude Natamycin Compositions Against *Botrytis* on Apples

This example demonstrates the antifungal effect of crude natamycin compositions against *Botrytis* on apple.

This experiment was performed as described in Example 18. Natamycin A and Natamycin E were used and data were recorded at different time points, as is indicated in Table 34.

TABLE 34

| | Efficacy (%) Days | | | |
|---|---|---|---|---|
| Treatment | 3 | 5 | 7 | 9 |
| Natamycin A | 93 | 77 | 79 | 74 |
| Natamycin E | 75 | 58 | 53 | 42 |
| Untreated control | 0 | 0 | 0 | 0 |
| Control without fungal infection | 100 | 100 | 100 | 100 |

From these data, it is clear that Natamycin A comprising cellular matter has a higher efficacy than Natamycin E which was purified.

Example 20

Antifungal Effect of Natamycin Comprising Cellular Matter Against *Botrytis* on Apples This experiment was performed as described in Example 19. Natamycin A and Natamycin E were used at different concentrations and data were recorded at different time points, as is indicated in Table 35.

TABLE 35

| Treatment | Efficacy (%) Days | | |
|---|---|---|---|
| | 3 | 5 | 7 |
| Natamycin A 100 ppm | 87 | 62 | 40 |
| Natamycin E 100 ppm | 84 | 41 | 12 |
| Natamycin A 2000 ppm | 100 | 93 | 72 |
| Natamycin E 2000 ppm | 100 | 62 | 50 |
| Untreated control | 0 | 0 | 0 |
| Control without fungal infection | 100 | 100 | 100 |

Natamycin A comprising cellular matter has a higher efficacy than Natamycin E which was purified.

Example 21

Efficacy Effect on *Rhizoctonia Solani* on Beans

This example demonstrates the effect of natamycin with proteins and starch on beans inoculated with *Rhizoctonia*

The trial was conducted inside a greenhouse. The soil was artificially inoculated with >10E6 colony forming units *Rhizoctonia solani* a week before sowing. The inoculation was done by mixing sporulating mycelium through the soil. The soil was inoculated with 1 petri dish blended in 50 ml water per liter of soil. In the week before sowing the soil was kept humid and warm to provide optimum growth conditions for the fungi. 100 seeds were sown per crate, and each crate represented one replication for each treatment. Every treatment had five replicates. Each treatment had a concentration of 2.5 gram of natamycin per 100 kg of seed, which equals about 10 ml of the formulation indicated below. At each assessment date, the numbers of healthy or diseased plants infected with *Rhizoctoni* a were counted per plot. Assessment was done on 3, 6, 13 and 21 days after sowing. The efficacy was calculated by the following equation:

Formulations included 250 gram/liter (g/l) of natamycin F, I and C; 25 g/l Atlas G 5002-L; 10 g/l MetaSperse 550S; 200 ppm Acticide MBS; 252 g/l glycerol; 6 g/l Rhodorsil 426R; 77 g/l of 2% Rhodopol 23 in water; and 480 g/l water. Because Natamycin G is 80% natamycin, the amount natamycin was reduced to 185 g/l, and 545 g/l of water was added.

Efficacy=((living plants treatment×100)/living plants untreated inoculated)-100.

The results are presented in Table 36 below:

TABLE 36

| | Efficacy Days after sowing | | | |
|---|---|---|---|---|
| | 3 | 6 | 13 | 21 |
| Untreated—inoculated | 0 | 0 | 0 | 0 |
| Formulation Natamycin F | 39.7 | 11.6 | 12.4 | 6.7 |
| Formulation Natamycin G | 61.1 | 11.9 | 19.7 | 19 |
| Formulation Natamycin I | 49.5 | 10.7 | 14.6 | 34.8 |
| Formulation Natamycin C | 42.4 | 11.1 | 14.8 | 28.9 |

Formulation natamycin F was purified and showed a lower efficacy on beans compared to formulations natamycin G, I and C, which all comprise cellular matter. It is noted that formulation natamycin G has a natamycin concentration of 80%, and formulations I and C have a natamycin concentration of 60%, compared to the 95% concentration natamycin in formulation natamycin F. The differences in concentrations was not compensated, rendering formulations natamycin G, I and C to have a higher efficacy than the purified Formulation Natamycin F.

Example 22

Stability of Natamycin in a Formulation with the Surfactants Tween 20 and Emulsogen SF8 with and without Structuring Agent A premix of natamycin was made as indicated in Table 37. The ingredients of the natamycin premix were milled over a Dyno-mill® (Glen Mills Inc. Clifton, N.J.) until a particle size between 2 to 3 μm was obtained.

TABLE 37

| Natamycin premix | g/l |
|---|---|
| Natamycin 95% | 263 |
| Di-sodium fumarate pH 7 buffer | 100 |
| Kathon | 40 ppm |
| Water | 637 |
| Total | 1000 |

A similar premix was made for crude natamycin batches.

To this Natamycin premix, the other ingredients mentioned in Table 38 were added. The obtained formulation was mixed until a homogeneous solution was obtained. For stability assessment the following parameterswere analyzed:

viscosity (expressed as mPa·s), particle size (μm), sedimentation (of natamycin crystals)

phase separation (formation of a liquid top or bottom layer).

The formulations were considered stabile if the parameters remained constant after 2 weeks incubation 54° C.?) (no increase etyc.

A first formulation was made with the surfactants polyethylene glycol sorbitan monolaurate (Tween 20 0; Sigma) and sodium di(2-ethylhexyl) sulfosuccinate (Emulsogen SF8; Clariant) with and without the structuring agent xantham gum (Rhodopol 23, Rhodia).

TABLE 38

| | 100 g/l Nata | 100 g/l Nata |
|---|---|---|
| Natamycin 25% w/w premix | 400 | 400 |
| Surfactant Tween 20 | 50 | 50 |
| Surfactant Emulsogen SF8 50% | 50 | 50 |

TABLE 38-continued

|  | 100 g/l Nata | 100 g/l Nata |
| --- | --- | --- |
| Glycerol | 300 | 300 |
| Anti-foam Rhodorsil 426R | 5 | 5 |
| Structuring agent Rhodopol 23 (2%)[1] | 0 | 58 |
| Water | 245 | 187 |
| Totals | 1050 | 1050 |
| Stability[2] | − | + |

[1]means addition of a 2% Rhodopol solution in water,
[2]− is unstable; + is stable suspension concentrate formulation.

The effect of 5 different classes of structuring agents was tested in combination with surfactants. More than 1 compound was tested for some classes of structuring agents. In total 9 tests were performed.

Rhodorsil 426R (poly[oxy(dimethylsilylene)]; Bluestar Silicones, Lyon, France) is an antifoaming agent.

TABLE 39

Stability of natamycin a formulation with the surfactants Tween 20 and Metasperse 550 S (Croda) with the structuring agent Rhodopol 23.

|  | 100 g/l Nata | 100 g/l Nata |
| --- | --- | --- |
| Natamycin premix 40% | 250 | 250 |
| Tween 20 | 25 | 25 |
| Chitosan | 20 | 20 |
| HCl 36% | 10 | 10 |
| Calcium-Lignosulfonate | 100 | 100 |
| MetaSperse 550 S | 7.5 | 7.5 |
| Glycerol | 252 | 252 |
| Rhodorsil 426R | 5 | 5 |
| Rhodopol 23 (2%) | 0 | 58 |
| Water | 352.5 | 294.5 |
| Totals | 1022 | 1022 |
| Stability | − | + |

Conclusion: a combination of the surfactants Tween 20 and Metasperse 550 S can be used to make stabile crude natamycin formulation if a structuring agent is present (Rhodopol 23).

TABLE 40

Stability of natamycin in a formulation with surfactants Atlas G 5002-L and MetaSperse 550 S, with and without the structuring agent Rhodopol 23.

|  | 150 g/l Nata | 150 g/l Nata |
| --- | --- | --- |
| Natamycin crude 60% | 250 | 250 |
| Atlas G 5002-L | 25 | 25 |
| MetaSperse 550 S | 10 | 10 |
| Isocil | 50 ppm | 50 ppm |
| Glycerol | 252 | 252 |
| Rhodorsil 426R | 6 | 6 |
| Rhodopol 23 (2% in water) | 55 | 0 |
| Water | 502 | 557 |
| Totals | 1100 | 1100 |

Isocil (5-bromo-3-isopropyl-6-methyluracil; Lonza, Breda, the Netherlands) was used as a preservative.

The formulation with Atlas G 5002-L and MetaSperse 550 S was generated by adding glycerol, Isocil, Atlas G 5002-L and MetaSperse 550 S to the water fraction. Next, 80% of the amount of anti-foam Rhodorsil 426R was added. Hereafter, natamycin was gently added and left mixing for 30 minutes. The formulation was milled on a Dispermat for 30 minutes to an average particle size of 1.5 μm. Hereafter, the remaining part of Rhodorsil 426R was added. Finally, Rhodopol 23 was slowly added.

Result: the obtained formulation with Rhodopol 23 was stable. No persistent foam and no sediment were observed. A formulation without Rhodopol 23 was not stable.

TABLE 41

|  |  | Particle size | | viscosity | |
| --- | --- | --- | --- | --- | --- |
|  |  | d50 (um) | d90 (um) | (S62) | |
|  |  |  |  | R12 | R60 |
| RT (t0) | pH | 1.6 | 4.4 | 417 | 155 |
| 2 weeks 54° C.* | 6.65 | 1.6 | 4.8 | 440 | 178 |
| 2 weeks 4° C.** | 7.28 | 1.6 | 4.6 | 435 | 160 |
| 2 months 40° C.*** | 6.99 | 1.6 | 4.7 | 422 | 160 |

*3 mm top layer on 14 cm (2.1%)
**2 mm top layer on 14 cm (1.4%)
***2 mm top layer on 14 cm (1.4%)

Conclusion: a combination of the surfactants Atlas G 5002-L and MetaSperse 550 S with the structuring agent Rhodopol 23 does lead to a stabile formulation. A formulation without Rhodopol 23 was not stabile.

TABLE 42

Stability of natamycin in a formulation with different amounts of surfactants Atlas G 5002-L and MetaSperse 550 S, with and without the structuring agent Rhodopol 23.

|  | 60 g/l Nata |
| --- | --- |
| Natamycin crude 60% | 100 |
| Atlas G 5002-L | 20 |
| MetaSperse 550 S | 8 |
| Acticide | 50 ppm |
| Glycerol | 252 |
| Rhodorsil 426R | 6 |
| Rhodopol 23 (2% in water) | 77 |
| Water | 637 |
| Totals | 1100 |

Acticide (2-methylisothiazol-3(2H)-one; Thor, Canterbury, England) was used as a preservative.

TABLE 43

|  |  | Average particle size | | Viscosity (S62) | |
| --- | --- | --- | --- | --- | --- |
|  | pH | d50 (um) | d90 (um) | 12 rpm | 60 rpm |
| RT (t0) | 7.4 | 1.7 | 5.3 | 345 | 125 |
| 2 weeks 54° C. | 7.32 | 1.7 | 5.1 | 310 | 116 |
| 1 week 4° C. | 7.33 | 1.7 | 5.1 | 342 | 126 |
| 2 months 40° C. | 7.40 | 1.8 | 5.1 | 324 | 119 |

Conclusion: a combination of the surfactants Atlas G 5002-L+MetaSperse 550 S with the structuring agent Rhodopol 23 leads to stabile formulation, while a formulation without Rhodopol 23 was not stabile.

The experiment was repeated with a different batch of natamycin, provided by a different supplier.

TABLE 44

| | 100 g/l Nata |
|---|---|
| Natamycin Freda 95% | 105.3 |
| Atlas G 5002-L | 20 |
| MetaSperse 550 S | 8 |
| Acticide | 50 ppm |
| Glycerol | 252 |
| Rhodorsil 426R | 6 |
| Rhodopol 23 (2% in water) | 77 |
| Water | 631.7 |
| Totals | 1100 |

Results: no persistent foam was observed.

Conclusion: natamycin from different source+combination of the surfactants Atlas G 5002-L+MetaSperse 550 S with the structuring agent Rhodopol 23 leads to stabile formulation, while a formulation without Rhodopol 23 was not stabile.

Example 23

Stability of Natamycin in a Formulation with Atlas G 5002-L and MetaSperse 550S and Different Structuring Agents A formulation as depicted in Table 45 with Atlas G 5002-L and MetaSperse 550 S was generated by adding glycerol, Atlas G 5002-L and MetaSperse 550 S to the water fraction. Next, 5 g/l of the antifoam Rhodorsil 426 R was added. Hereafter, natamycin was gently added and left mixing for 30 minutes. The formulation was milled on a Dispermat for 30 minutes to an average particle size of 2 µm. Hereafter, the remaining 1 g/l of Rhodorsil 426R was added, followed by 200 ppm of Acticide MBS. Next, a structuring agent as indicated in Tables 46 and 47 was added, and the resulting suspension concentrate was stirred for three hours and left overnight. After 12 h of rest, formulations were stored undisturbed at 54° C. for 2 weeks. Viscosity was determined according to the CIPAC method MT192 at 12 rpm and 60 rpm using a Brookfiled DV-E viscometer.

TABLE 45

| Formulation constituents | |
|---|---|
| CF800-154 | G/l |
| Crude natamycin (natamycin H) | 250 |
| Atlas G 5002-L | 25 |
| MetaSperse 550S | 10 |
| Acticide MBS (200 ppm) | |
| Glycerol | 252 |
| Rhodorsil 426R | 6 |
| Structural agent | See below |
| Water | 557 |
| Total | 1100 |

TABLE 46

| List of structural agents | | |
|---|---|---|
| Structuring agent | Name | Supplier |
| Xanthan gum | Rhodopol 23 | Rhodia |
| Natural mixture of glycoproteins and polysaccharides | Arabic gum | Carl Roth |
| Attapulgite | Attagel 30 | BASF |
| Attapulgite | Attagel 50 | BASF |
| Non-ionic polyurethane based agent | Borchi gel 0626 | OMG Borchers GmbH |
| Polyester block co-polymer | Rheostrux 100 PW | Croda |
| Succinoglycan gum | Rheozan | Rhodia |

TABLE 47

| Amounts of structuring agents used | | |
|---|---|---|
| structuring agent | m. struc. agent (g) | % struct. Agent (w/w) |
| Rhodopol 23 (2% sol.) | 18 | 0.14 |
| Arabic gum | 2.4 | 0.95 |
| Attagel 30 | 2.5 | 1.00 |
| Attagel 50 | 2.5 | 1.00 |
| Borchi gel 0626 | 1.4 | 0.56 |
| Borchi gel Thixo 2 | 1.3 | 0.52 |
| Rheostrux 100PW | 2.5 | 0.99 |
| Rheostrux 200PA | 2.6 | 1.03 |
| Rheozan | 2.7 | 1.07 |

Viscosity of the formulated mixtures was determined after accelerated stability storage test. Results are shown in Table 48.

TABLE 48

| Viscosity tests of formulations | | |
|---|---|---|
| Formulation | η 12 rpm (mPa · s) | η 60 rpm (mPa · s) |
| Rhodopol 23 (2% sol.) | 1290 | 504 |
| Arabic gum | 800 | 278 |
| Attagel 30 | 100 | 77 |
| Attagel 50 | 137 | 103 |
| Borchi gel 0626 | 1590 | 1090 |
| Rheostrux 100PW | 700 | 370 |
| Rheozan | 1400 | 268 |

There were no big differences observed between the tested agents in term of colloidal stability. In all cases the top layer was very small.

There were no big differences observed between the tested agents in term of average particle sizes. As is depicted in Table 49, the average particle size was about 2 micrometer in all cases after storage for 2 weeks at 54° C.

TABLE 49

| Particle sizes. | | |
|---|---|---|
| Structuring agent | d0.5 (µm) | d0.9 (µm) |
| Rhodopol 23 (2% sol.) | 2.1 | 9.0 |
| Arabic gum | 2.1 | 8.5 |
| Attagel 30 | 2.3 | 12.9 |
| Attagel 50 | 2.2 | 9.5 |
| Borchi gel 0626 | 2.0 | 8.1 |
| Rheostrux 100PW | 2.0 | 8.0 |
| Rheozan | 2.0 | 8.5 |

Conclusion: natamycin from different source+combination of the surfactants Atlas G 5002-L+MetaSperse 550 S with different structuring agents resulted in a stable formulation.

The invention claimed is:

1. A natamycin composition comprising natamycin, or a salt thereof,
   wherein the natamycin composition has an average particle size of about 6 μm or less and a surface area of less than 6 $m^2/g$, as determined by Brunauer, Emmett and Tellers (BET) analysis, and
   wherein the natamycin composition is milled.

2. The natamycin composition of claim 1, wherein the natamycin composition has a surface area of less than 2 $m^2/g$, as determined by BET analysis.

3. The natamycin composition of claim 1, further comprising at least one surfactant and at least one structuring agent.

4. The natamycin composition of claim 1, wherein the natamycin composition further comprises 1-40% (w/w) of cellular matter comprising protein.

5. The natamycin composition of claim 1, comprising natamycin, or a salt thereof, a structuring agent and a surfactant, wherein the natamycin composition further comprises 1-40% (w/w) of cellular matter comprising protein.

6. The natamycin composition of claim 1, wherein the natamycin composition is produced by fermenting biomass by a fermentation organism.

7. The natamycin composition of claim 1, wherein the composition further comprises at least one wetting agent, or at least one dispersing agent, or a combination thereof.

8. A fungicide, comprising a natamycin composition of claim 1.

9. The fungicide of claim 8, further comprising at least one antifoaming agent, at least one thickening agent, at least one stabilizing agent, or glycerol, or any combinations thereof.

10. A method, comprising:
    contacting a plant or a fungus, or a part thereof, with a natamycin composition of claim 1 to treat the plant or fungus, or a part thereof.

11. A method, comprising:
    treating seeds with a natamycin composition of claim 1 to produce treated seeds; and
    germinating the treated seeds.

12. A method, comprising:
    contacting fruit with a natamycin composition of claim 1.

13. A method, comprising:
    contacting soil with a natamycin composition of claim 1.

14. A method, comprising:
    contacting a crop with a natamycin composition of claim 1.

15. The natamycin composition of claim 1, wherein the natamycin composition has an average particle size of about 2 μm.

16. The natamycin composition of claim 1, wherein natamycin content in the composition is about 60%.

17. The natamycin composition of claim 1, wherein the natamycin composition comprises natamycin methylester.

18. The natamycin composition of claim 1, wherein the natamycin composition is treated with organic solvent.

* * * * *